United States Patent [19]

Meyer et al.

[11] Patent Number: 5,071,761

[45] Date of Patent: Dec. 10, 1991

[54] HYBRID INTERFERONS

[75] Inventors: François Meyer, Zürich; Albert Hinnen, Basel; Andreas Meister, Riehen; Markus G. Grütter, Hochwald; Sefik Alkan, Riehen, all of Switzerland

[73] Assignee: Ciba-Geigy Corporation, Yardsley, N.Y.

[21] Appl. No.: 381,444

[22] Filed: Jul. 18, 1989

Related U.S. Application Data

[62] Division of Ser. No. 871,059, Jun. 5, 1986, Pat. No. 4,885,166.

[30] Foreign Application Priority Data

| Jun. 11, 1985 | [GB] | United Kingdom | 8514722 |
| Jun. 11, 1985 | [GB] | United Kingdom | 8514723 |
| Jun. 11, 1985 | [GB] | United Kingdom | 8514724 |
| Jun. 11, 1985 | [GB] | United Kingdom | 8514725 |
| Jun. 11, 1985 | [GB] | United Kingdom | 8514726 |

[51] Int. Cl.$^5$ ............... C12N 15/20; C12N 15/21; C12N 15/67; C12N 15/70; C12N 15/81

[52] U.S. Cl. .................. 435/243; 435/172.3; 435/69.5; 435/69.51; 435/252.3; 435/252.33; 435/255; 435/256; 435/320.1; 530/351; 935/194

[58] Field of Search .......... 530/351; 435/69.5.1, 435/69.1, 320, 252.3, 252.31-252.35, 811, 255, 256, 320.1; 800/2; 536/27; 430/142

[56] References Cited

U.S. PATENT DOCUMENTS

| 4,414,150 | 11/1983 | Goeddel | 530/351 |
| 4,456,748 | 6/1984 | Goeddel | 536/27 |
| 4,569,908 | 2/1986 | Mark et al. | 435/69.51 |
| 4,716,217 | 12/1987 | Caruthers et al. | 530/351 |

FOREIGN PATENT DOCUMENTS

| 0032134 | 7/1981 | European Pat. Off. | 435/172.3 |
| 0130564 | 1/1985 | European Pat. Off. | |
| 0130565 | 1/1985 | European Pat. Off. | |
| 0130566 | 1/1985 | European Pat. Off. | |
| 0131816 | 1/1985 | European Pat. Off. | |
| 0163993 | 2/1985 | European Pat. Off. | |
| 0141484 | 5/1985 | European Pat. Off. | 435/172.3 |
| 0146903 | 7/1985 | European Pat. Off. | 435/172.3 |
| 0173935 | 3/1986 | European Pat. Off. | |
| 2108510 | 5/1983 | United Kingdom | |

OTHER PUBLICATIONS

Weck et al, Nucl. Acids Res. vol. 9, No. 22 pp. 6153-6166 (1981).
Weber et al, Nucl. Acids Res. vol. 11, No. 16 pp. 5661-5669 (1983).
Streuli et al, Proc. Natl. Acad. Sci, U.S.A. vol. 78, No. 5 pp. 2848-2852 (1981).
Rehberg et al, J. Biol. Chem. vol. 257, No. 19 pp. 11497-11502 (1982).
Franke et al, DNA vol. 1, No. 3 pp. 223-230 (1982).
Pestka, Arch. Biochem. Biophys. vol. 221, No. 1 pp. 1-37 (1983).
Pestka, Scientific American vol. 249 No. 2, pp. 29-35 (1983).
Chem. Abstr. 105:131876z (1986).

*Primary Examiner*—James Martinell,
*Attorney, Agent, or Firm*—Steven R. Lazar; JoAnn Villamizar

[57] ABSTRACT

Novel hybrid interferons are produced which are derived from lymphoblastoid interferons α-2 and α-3 belonging to the interferon αB and αD groups, respectively. The novel hybrid interferons possess valuable antiviral and antiproliferative properties.

11 Claims, 5 Drawing Sheets

|  | 1 |  |  |  |  |  |  |  |  |  |  |  |  |  |  | 16 |
|---|---|---|---|---|---|---|---|---|---|---|---|---|---|---|---|---|
| α-2 | CYS | ASP | LEU | PRO | GLN | THR | HIS | SER | LEU | GLY | ASN | ARG | ARG | ALA | LEU | ILE |
| α-3 |  |  |  |  | GLU |  |  |  |  | ASP |  |  |  | THR |  | MET |
|  |  |  |  |  |  |  |  |  |  |  |  |  |  |  |  | 32 |
| α-2 | LEU | LEU | ALA | GLN | MET | ARG | ARG | ILE | SER | PRO | PHE | SER | CYS | LEU | LYS | ASP |
| α-3 |  |  |  |  |  | SER |  |  |  |  |  | SER |  |  |  | MET |
|  |  |  |  |  |  |  |  |  |  |  |  |  |  |  |  | 48 |
| α-2 | ARG | HIS | ASP | PHE | GLU | PHE | PRO | GLN | GLU | GLU | PHE | ASP | ASP | LYS | GLN | PHE |
| α-3 |  |  |  |  | GLY |  |  |  |  |  |  |  | GLY | ASN |  |  |
|  |  |  |  |  |  |  |  |  |  |  | 60 |  |  |  |  | 64 |
| α-2 | GLN | LYS | ALA | GLN | ALA | ILE | SER | VAL | LEU | HIS | GLU | MET | ILE | GLN | GLN | THR |
| α-3 |  |  |  | PRO |  |  |  |  |  |  |  | LEU |  |  |  | ILE |
|  |  |  |  |  |  |  |  |  |  |  |  |  |  |  |  | 80 |
| α-2 | PHE | ASN | LEU | PHE | SER | THR | LYS | ASP | SER | SER | ALA | ALA | LEU | ASP | GLU | THR |
| α-3 |  |  |  |  |  | THR |  |  |  |  |  |  | TRP |  |  | ASP |
|  |  |  |  |  |  |  |  |  |  |  |  |  | 92 |  |  | 96 |
| α-2 | LEU | LEU | ASP | GLU | PHE | TYR | ILE | GLU | LEU | ASP | GLN | GLN | LEU | ASN | ASP | LEU |
| α-3 |  |  | LYS |  |  | CYS | THR |  |  |  | TYR |  |  |  |  |  |
|  |  |  |  |  |  |  |  |  |  |  |  |  |  |  |  | 112 |
| α-2 | GLU | SER | CYS | VAL | MET | GLN | GLU | VAL | GLY | VAL | ILE | GLU | SER | PRO | LEU | MET |
| α-3 |  | ALA |  |  |  |  | GLU | ARG |  | GLY |  |  | THR |  |  |  |
|  |  |  |  |  |  |  |  |  |  |  |  |  |  |  |  | 128 |
| α-2 | TYR | GLU | ASP | SER | ILE | LEU | ALA | VAL | ARG | LYS | TYR | PHE | GLN | ARG | ILE | THR |
| α-3 | ASN | ALA |  |  |  |  |  |  |  | LYS |  |  |  | ARG |  |  |
|  |  |  |  |  |  |  |  |  |  |  |  |  |  |  |  | 144 |
| α-2 | LEU | TYR | LEU | THR | GLU | LYS | LYS | TYR | SER | SER | CYS | ALA | TRP | GLU | VAL | VAL |
| α-3 |  |  |  |  |  |  |  |  |  | PRO |  |  |  |  |  |  |
|  |  |  |  |  | 150 |  |  |  |  |  |  |  |  |  |  | 160 |
| α-2 | ARG | ALA | GLU | ILE | MET | ARG | SER | PHE | SER | LEU | SER | ILE | ASN | LEU | GLN | LYS |
| α-3 |  |  |  |  |  |  |  | LEU |  |  |  | THR |  |  |  | GLU |
|  |  |  |  |  |  | 166 |  |  |  |  |  |  |  |  |  |  |
| α-2 | ARG | LEU | LYS | SER | LYS | GLU |  |  |  |  |  |  |  |  |  |  |
| α-3 |  | ARG | ARG |  |  |  |  |  |  |  |  |  |  |  |  |  |

FIG. 1

```
                                                                        16
        1   Sau3A
α-2  TGT GAT CTG CCT CAG ACT CAC AGC CTG GGT AAC AGG AGG GCC TTG ATA
α-3  TGT GAT CTC CCT GAG ACC CAC AGC CTG GAT AAC AGG AGG ACC TTG ATG
                                                                        32
α-2  CTC CTG GCA CAA ATG CGA AGA ATC TCT CCT TTC TCC TGC CTG AAG GAC
α-3  CTC CTG GCA CAA ATG AGC AGA ATC TCT CCT TCC TCC TGT CTG ATG GAC
                                                                        48
α-2  AGA CAT GAC TTT GAA TTC CCC CAG GAG GAG TTT GAT GAT AAA CAG TTC
α-3  AGA CAT GAC TTT GGA TTT CCC CAG GAG GAG TTT GAT GGC AAC CAG TTC
                                            Sau3A                       64
α-2  CAG AAG GCT CAA GCC ATC TCT GTC CTC CAT GAG ATG ATC CAG CAG ACC
α-3  CAG AAG GCT CCA GCC ATC TCT GTC CTC CAT GAG CTG ATC CAG CAG ATC
                                                                        80
α-2  TTC AAC CTC TTC AGC ACA AAG GAC TCA TCT GCT GCT TTG GAT GAG ACC
α-3  TTC AAC CTC TTT ACC ACA AAA GAT TCA TCT GCT GCT TGG GAT GAG GAC
                                                PvuII                   96
α-2  CTT CTA GAT GAA TTC TAC ATC GAA CTT GAC CAG CAG CTG AAT GAC CTG
α-3  CTC CTA GAC AAA TTC TGC ACC GAA CTC TAC CAG CAG CTG AAT GAC TTG
                                                                       112
α-2  GAG TCC TGT GTG ATG CAG GAA GTG GGG GTG ATA GAG TCT CCC CTG ATG
α-3  GAA GCC TGT GTG ATG CAG GAG GAG AGG GTG GGA GAA ACT CCC CTG ATG
                                                                       128
α-2  TAC GAG GAC TCC ATC CTG GCT GTG AGG AAA TAC TTC CAA AGA ATC ACT
α-3  AAT GCG GAC TCC ATC TTG GCT GTG AAG AAA TAC TTC CGA AGA ATC ACT
                                                                       144
α-2  CTA TAT CTG ACA GAG AAG AAA TAC AGC TCT TGT GCC TGG GAG GTT GTC
α-3  CTC TAT CTG ACA GAG AAG AAA TAC AGC CCT TGT GCC TGG GAG GTT GTC
                    Sau3A                                              160
α-2  AGA GCA GAA ATC ATG AGA TCC TTC TCT TTA TCA ATC AAC TTG CAA AAA
α-3  AGA GCA GAA ATC ATG AGA TCC CTC TCT TTA TCA ACA AAC TTG CAA GAA
     166
α-2  AGA TTG AAG AGT AAG GAA TGA GACCTGGTACAACACGGAAATGATTCTTATAGACT
α-3  AGA TTA AGG AGG AAG GAA TAA CACCTGGTCCAACATGAAACAATTCTTATTGACTC

α-2  AATACAGCAGCTCACACTTCGACAAGTTGTGCTCTTTCAAAGACCCTTGTTTCTGCCAAAACC
α-3  ATATACCAGGTCACGCTTTCATGAATTCTGCCATTTCAAAGACTCTCACTTCTGCTATAACTA

α-2  ATGCTATGTTTTGAATCAAATGTGTCAAGTGTTTTCAGGAGTGTTAAGCAACATCCTGTT
α-3  TGACCATGCTGATAAACTGATTTATCTATTTAAATATTTATTTAGCTATTCATAAGATTT

PvuII                                       Sau3A
α-2  CAGCTGTATGGGCACTAGTCCCTTACAGATGACCATGCTGATGGATCTATTCATCTATTTATT
α-3  AAATTATTTTTGTTCATATAACATCATGTCCATCTTTACACTGTGGTTAGTGTAATAAAACAT

α-2  TAAATCTTTATTTAGTTAACTATCTATAGGGCTTAAATTAGTTTTGTTCATATTATATTATGT
α-3  GTTCCTTATATTTACTCAAATTCATTATTTT.....

α-2  GAACTTTTACATTGTGAATTGTGTAACAAAAACATGTTCTTTATATTTATTATTTTGCCTTGT

α-2  TTATTAAATTTTTACTATAG...
```

α-2 ...GAGACAATAACCCTGATAAATGCTTCAATAATATTGAAAAAGGAAGAGTAATG
α-3 ...GAGACAATAACCCTGATAAATGCTTCAATAATATTGAAAAAGGAAGAGTAATG

FIG. 2

HYBRID INTERFERONS

This is a divisional of application Ser. No. 871,059, filed on June 5, 1986, which issued on Dec. 5, 1989 as U.S. Pat. No. 4,885,166.

The invention concerns novel hybrid interferons, the microbial production thereof via recombinant DNA technology, and their use for the treatment of viral and neoplastic diseases.

The interferons ("IFNs") are a family of polypeptides secreted by a large variety of eukaryotic cells upon exposure to various mitogens and viruses. The interferons have been classified by their chemical and biological characteristics into three groups: IFN-α, IFN-β, and IFN-γ. IFN-α and β genes are expressed predominantly in cells treated with viruses, viral constituents and double stranded RNA. IFN-γ on the other hand, is synthesized in response to mitogens.

Human IFN-α is coded for by a gene family comprising at least 15 non-allelic genes. Human IFN-β and human IFN-γ are encoded by single genes. The primary translation product of IFN-α comprises 189 amino acids (except IFN-$\alpha_2$: 188 amino acids), from which a signal peptide of 23 amino acids is removed by post-translational modification. Human IFN-β and human IFN-γ consist of 187 and 186 amino acids from which 21 or 20 amino acids constituting the signal peptides are removed. The amino acid sequence homology among IFN-α subtypes is 80–85% whereas the homology between IFN-β and IFN-α is about 30–40%. IFN-γ shows only single amino acid homologies with IFN-α, corresponding to 12% identical residues.

The IFNs exhibit antiviral, immunomodulatory, as well as cytotoxic activities. It has been demonstrated that IFN-α subtypes (e.g. IFN-$\alpha_2$, IFN-$\alpha_1$) show different target cell specificities. The antiviral activity of IFN-$\alpha_2$ and IFN-$\alpha_1$ is about the same on bovine (MDBK) cells, but IFN-$\alpha_2$ is seven times more effective than IFN-$\alpha_1$ on human (WISH) cells, and 30 times less effective than IFN-$\alpha_1$ in protecting mouse (L 929) cells. [M. Streuli et al., Proc. Natl. Acad. Sci. U.S.A. 78, 2848 (1981)]. The evidence that members of the multigene IFN-α family vary in the extent and specificity of their antiviral activity has been confirmed by results obtained from some IFN-α "hybrids" (cf. EP 32134, U.S. Pat. No. 4,414,150). These "hybrids" have been constructed by cleaving two genes coding for interferon-α subtypes with the restriction enzyme PvuII (or, in two cases, with BglII) and cross-ligating the resulting fragments such that the DNA sequence coding for the amino terminal part of one IFN gene was fused to the DNA sequence coding for the carboxy terminal part of the other IFN gene. Although these hybrid interferons exhibit changes in target cell specificity as compared to the parent interferons it was not demonstrated that there was any attenuation or any restriction of any of the three interferon activities. Such attenuation or restriction may be desirable, for example, in clinical application where it is desirable to focus interferon therapy on a particular problem such as viral infection, without the possibility of complicating factors resulting from other activities of the administered interferon.

It is thus an object of the present invention to provide novel hybrid interferons which show more specific biological activities resulting from the selective or predominant activation of only some of the interferon-induced biochemical pathways, and/or in which some of the undesired side effects of natural interferons which limit their use, such as influenza-like symptoms (e.g. fever, headache and fatigue), gastrointestinal disturbances, decrease of blood pressure and loss of hair, are excluded or reduced.

The hybrid interferons according to the invention are derived from human lymphoblastoid interferon LyIFN-α-2 having the sequence

```
CYS ASP LEU PRO GLN THR HIS SER LEU GLY ASN ARG ARG ALA LEU ILE LEU
LEU ALA GLN MET ARG ARG ILE SER PRO PHE SER CYS LEU LYS ASP ARG HIS
ASP PHE GLU PHE PRO GLN GLU GLU PHE ASP ASP LYS GLN PHE GLN LYS ALA
GLN ALA ILE SER VAL LEU HIS GLU MET ILE GLN GLN THR PHE ASN LEU PHE
SER THR LYS ASP SER SER ALA ALA LEU ASP GLU THR LEU LEU ASP GLU PHE
TYR ILE GLU LEU ASP GLN GLN LEU ASN ASP LEU GLU SER CYS VAL MET GLN
GLU VAL GLY VAL ILE GLU SER PRO LEU MET TYR GLU ASP SER ILE LEU ALA
VAL ARG LYS TYR PHE GLN ARG ILE THR LEU TYR LEU THR GLU LYS LYS TYR
SER SER CYS ALA TRP GLU VAL VAL ARG ALA GLU ILE MET ARG SER PHE SER
LEU SER ILE ASN LEU GLN LYS ARG LEU LYS SER LYS GLU
``` and human lymphoblastoid interferon LyIFN-α-3 having the sequence

```
CYS ASP LEU PRO GLU THR HIS SER LEU ASP ASN ARG ARG THR LEU MET LEU
LEU ALA GLN MET SER ARG ILE SER PRO SER SER CYS LEU MET ASP ARG HIS
ASP PHE GLY PHE PRO GLN GLU GLU PHE ASP GLY ASN GLN PHE GLN LYS ALA
PRO ALA ILE SER VAL LEU HIS GLU LEU ILE GLN GLN ILE PHE ASN LEU PHE
THR THR LYS ASP SER SER ALA ALA TRP ASP GLU ASP LEU LEU ASP LYS PHE
CYS THR GLU LEU TYR GLN GLN LEU ASN ASP LEU GLU ALA CYS VAL MET GLN
GLU GLU ARG VAL GLY GLU THR PRO LEU MET ASN ALA ASP SER ILE LEU ALA
VAL LYS LYS TYR PHE ARG ARG ILE THR LEU TYR LEU THR GLU LYS LYS TYR
SER PRO CYS ALA TRP GLU VAL VAL ARG ALA GLU ILE MET ARG SER LEU SER
LEU SER THR ASN LEU GLN GLU ARG LEU ARG ARG LYS GLU
```

These interferons as well as methods for the preparation thereof have been described in European Patent Application No. 76,489. LyIFN-α-2 is related to (but not identical with) human leukocyte interferon LeIF-αB (cf. U.S. Pat. No. 4,414,150) and has a specific activity on primary calf kidney cells and on human embryonic foreskin cells (HEF, each infected with vesicular stomatitis virus) of $1.85 \cdot 10^8$ IU/mg and $2.45 \cdot 10^8$ IU/mg, respectively. LyIFN-α-3 is related to (but not identical with) human leukocyte interferon LeIF-αD (cf. U.S. Pat. No. 4,414,150) and has a specific activity on calf cells and HEF cells (as above) of $1.32 \cdot 10^8$ IU/mg and $3.7 \cdot 10^6$ IU/mg, respectively. Furthermore, LyIFN-α-3 has a higher thermostability and lower antiproliferative activity than LyIFN-α-2.

It is a particular object of the present invention to provide LyIFN-α-2/α-3 hybrid polypeptides which combine the high antiviral titre and/or the higher antiproliferative activity on human cells of LyIFN-α-2 and the high thermostability of LyIFN-α-3.

Especially the invention relates to a hybrid interferon polypeptide having an amino acid sequence composed of two to four sub-sequences corresponding in amino acid identity and number to sub-sequences of human lymphoblastoid interferons LyIFN-α-2 and LyIFN-α-3, said hybrid interferon polypeptide being selected from the group consisting of a polypeptide having an amino acid sequence consisting of amino acids 1 to 150 of LyIFN-α-2 and amino acids 151 to 166 of LyIFN-α-3, a polypeptide having an amino acid sequence consisting of amino acids 1 to 92 of LyIFN-α-2, amino acids 93 to 150 of LyIFN-α-3 and amino acids 151 to 166 of LyIFN-α-2, and a polypeptide having an amino acid sequence consisting of amino acids 1 to 60 of LyIFN-α-2, amino acids 61 to 92 of LyIFN-α-3, amino acids 93 to 150 of LyIFN-α-2 or of LyIFN-α-3 and amino acids 151 to 166 of LyIFN-α-2 or of LyIFN-α-3.

More specifically, the invention relates to the hybrid interferon "$B_1B_2B_3D_4$" having the formula

```
CYS ASP LEU PRO GLN THR HIS SER LEU GLY ASN ARG ARG ALA LEU ILE LEU      (I)
LEU ALA GLN MET ARG ARG ILE SER PRO PHE SER CYS LEU LYS ASP ARG HIS
ASP PHE GLU PHE PRO GLN GLU GLU PHE ASP ASP LYS GLN PHE GLN LYS ALA
GLN ALA ILE SER VAL LEU HIS GLU MET ILE GLN GLN THR PHE ASN LEU PHE
SER THR LYS ASP SER SER ALA ALA LEU ASP GLU THR LEU LEU ASP GLU PHE
TYR ILE GLU LEU ASP GLN GLN LEU ASN ASP LEU GLU SER CYS VAL MET GLN
GLU VAL GLY VAL ILE GLU SER PRO LEU MET TYR GLU ASP SER ILE LEU ALA
VAL ARG LYS TYR PHE GLN ARG ILE THR LEU TYR LEU THR GLU LYS LYS TYR
SER SER CYS ALA TRP GLU VAL VAL ARG ALA GLU ILE MET ARG SER LEU SER
LEU SER THR ASN LEU GLN GLU ARG LEU ARG ARG LYS GLU,
``` to the hybrid interferon "$B_1B_2D_3B_4$" having the formula

```
CYS ASP LEU PRO GLN THR HIS SER LEU GLY ASN ARG ARG ALA LEU ILE LEU      (II)
LEU ALA GLN MET ARG ARG ILE SER PRO PHE SER CYS LEU LYS ASP ARG HIS
ASP PHE GLU PHE PRO GLN GLU GLU PHE ASP ASP LYS GLN PHE GLN LYS ALA
GLN ALA ILE SER VAL LEU HIS GLU MET ILE GLN GLN THR PHE ASN LEU PHE
SER THR LYS ASP SER SER ALA ALA LEU ASP GLU THR LEU LEU ASP GLU PHE
TYR ILE GLU LEU ASP GLN GLN LEU ASN ASP LEU GLU ALA CYS VAL MET GLN
GLU GLU ARG VAL GLY GLU THR PRO LEU MET ASN ALA ASP SER ILE LEU ALA
VAL LYS LYS TYR PHE ARG ARG ILE THR LEU TYR LEU THR GLU LYS LYS TYR
SER PRO CYS ALA TRP GLU VAL VAL ARG ALA GLU ILE MET ARG SER PHE SER
LEU SER ILE ASN LEU GLN LYS ARG LEU LYS SER LYS GLU,
``` to the hybrid interferon "$B_1D_2B_3D_4$" having the formula

```
CYS ASP LEU PRO GLN THR HIS SER LEU GLY ASN ARG ARG ALA LEU ILE LEU      (III)
LEU ALA GLN MET ARG ARG ILE SER PRO PHE SER CYS LEU LYS ASP ARG HIS
ASP PHE GLU PHE PRO GLN GLU GLU PHE ASP ASP LYS GLN PHE GLN LYS ALA
GLN ALA ILE SER VAL LEU HIS GLU MET ILE GLN GLN ILE PHE ASN LEU PHE
THR THR LYS ASP SER SER ALA ALA TRP ASP GLU ASP LEU LEU ASP LYS PHE
CYS THR GLU LEU TYR GLN GLN LEU ASN ASP LEU GLU SER CYS VAL MET GLN
GLU VAL GLY VAL ILE GLU SER PRO LEU MET TYR GLU ASP SER ILE LEU ALA
VAL ARG LYS TYR PHE GLN ARG ILE THR LEU TYR LEU THR GLU LYS LYS TYR
SER SER CYS ALA TRP GLU VAL VAL ARG ALA GLU ILE MET ARG SER LEU SER
LEU SER THR ASN LEU GLN GLU ARG LEU ARG ARG LYS GLU,
``` to the hybrid interferon "$B_1D_2D_3B_4$" having the formula

```
CYS ASP LEU PRO GLN THR HIS SER LEU GLY ASN ARG ARG ALA LEU ILE LEU      (IV)
LEU ALA GLN MET ARG ARG ILE SER PRO PHE SER CYS LEU LYS ASP ARG HIS
ASP PHE GLU PHE PRO GLN GLU GLU PHE ASP ASP LYS GLN PHE GLN LYS ALA
GLN ALA ILE SER VAL LEU HIS GLU MET ILE GLN GLN ILE PHE ASN LEU PHE
THR THR LYS ASP SER SER ALA ALA TRP ASP GLU ASP LEU LEU ASP LYS PHE
CYS THR GLU LEU TYR GLN GLN LEU ASN ASP LEU GLU ALA CYS VAL MET GLN
GLU GLU ARG VAL GLY GLU THR PRO LEU MET ASN ALA ASP SER ILE LEU ALA
VAL LYS LYS TYR PHE ARG ARG ILE THR LEU TYR LEU THR GLU LYS LYS TYR
SER PRO CYS ALA TRP GLU VAL VAL ARG ALA GLU ILE MET ARG SER PHE SER
LEU SER ILE ASN LEU GLN LYS ARG LEU LYS SER LYS GLU,
``` to the hybrid interferon "$B_1D_2D_3D_4$" having the formula

```
CYS ASP LEU PRO GLN THR HIS SER LEU GLY ASN ARG ARG ALA LEU ILE LEU      (V)
LEU ALA GLN MET ARG ARG ILE SER PRO PHE SER CYS LEU LYS ASP ARG HIS
ASP PHE GLU PHE PRO GLN GLU GLU PHE ASP ASP LYS GLN PHE GLN LYS ALA
GLN ALA ILE SER VAL LEU HIS GLU MET ILE GLN GLN ILE PHE ASN LEU PHE
THR THR LYS ASP SER SER ALA ALA TRP ASP GLU ASP LEU LEU ASP LYS PHE
CYS THR GLU LEU TYR GLN GLN LEU ASN ASP LEU GLU ALA CYS VAL MET GLN
GLU GLU ARG VAL GLY GLU THR PRO LEU MET ASN ALA ASP SER ILE LEU ALA
VAL LYS LYS TYR PHE ARG ARG ILE THR LEU TYR LEU THR GLU LYS LYS TYR
SER PRO CYS ALA TRP GLU VAL VAL ARG ALA GLU ILE MET ARG SER LEU SER
LEU SER THR ASN LEU GLN GLU ARG LEU ARG ARG LYS GLU,
``` and to the hybrid interferon "$B_1D_2B_3B_4$" having the formula (VI)

CYS ASP LEU PRO GLN THR HIS SER LEU GLY ASN ARG ARG ALA LEU ILE LEU
LEU ALA GLN MET ARG ARG ILE SER PRO PHE SER CYS LEU LYS ASP ARG HIS
ASP PHE GLU PHE PRO GLN GLU GLU PHE ASP ASP LYS GLN PHE GLN LYS ALA
GLN ALA ILE SER VAL LEU HIS GLU MET ILE GLN GLN ILE PHE ASN LEU PHE
THR THR LYS ASP SER SER ALA ALA TRP ASP GLU ASP LEU LEU ASP LYS PHE
CYS THR GLU LEU TYR GLN GLN LEU ASN ASP LEU GLU SER CYS VAL MET GLN
GLU VAL GLY VAL ILE GLU SER PRO LEU MET TYR GLU ASP SER ILE LEU ALA
VAL ARG LYS TYR PHE GLN ARG ILE THR LEU TYR LEU THR GLU LYS LYS TYR
SER SER CYS ALA TRP GLU VAL VAL ARG ALA GLU ILE MET ARG SER PHE SER
LEU SER ILE ASN LEU GLN LYS ARG LEU LYS SER LYS GLU.

The most preferred hybrid interferons according to the invention are "$B_1D_2D_3D_4$" (V) and "$B_1B_2D_3B_4$" (II).

A hybrid interferon according to the invention can be prepared by recombinant DNA technique comprising the steps, for example, of a) preparing a DNA comprising the structural gene coding for said hybrid interferon by in vitro recombination at the sites corresponding to amino acids 60, 92 and 150, respectively, of interferons LyIFN-α-2 and LyIFN-α-3 or by chemical DNA synthesis and incorporating the obtained DNA into an appropriate expression vector,
b) transferring the obtained hybrid vector carrying the hybrid IFN structural gene into a recipient host,
c) selecting transformed hosts from untransformed hosts, usually by culturing under such conditions where only the transformed hosts survive,
d) culturing the transformed hosts under conditions which allow expression of the hybrid IFN structural gene, and
e) isolating the expressed hybrid IFN.

The methods applied will become more apparent from the detailed description which follows and from the accompanying drawings in which:

BRIEF DESCRIPTION OF THE DRAWINGS

FIG. 1 compares the amino acid sequences of mature LyIFN-α-2 and LyIFN-α-3. Only those amino acids of LyIFN-α-3 which differ from corresponding amino acids of LyIFN-α-2 are depicted. The amino acid sequence of LyIFN-α-3 is otherwise identical to that of LyIFN-α-2.

FIG. 2 depicts the nucleotide sequences of the coding regions and parts of the 3'extracistronic regions of LyIFN-α-2 and LyIFN-α-3. The ATG translation initiation codons, the termination triplets and convenient restriction sites are underlined. The coding triplets are numbered.

Figure 3:
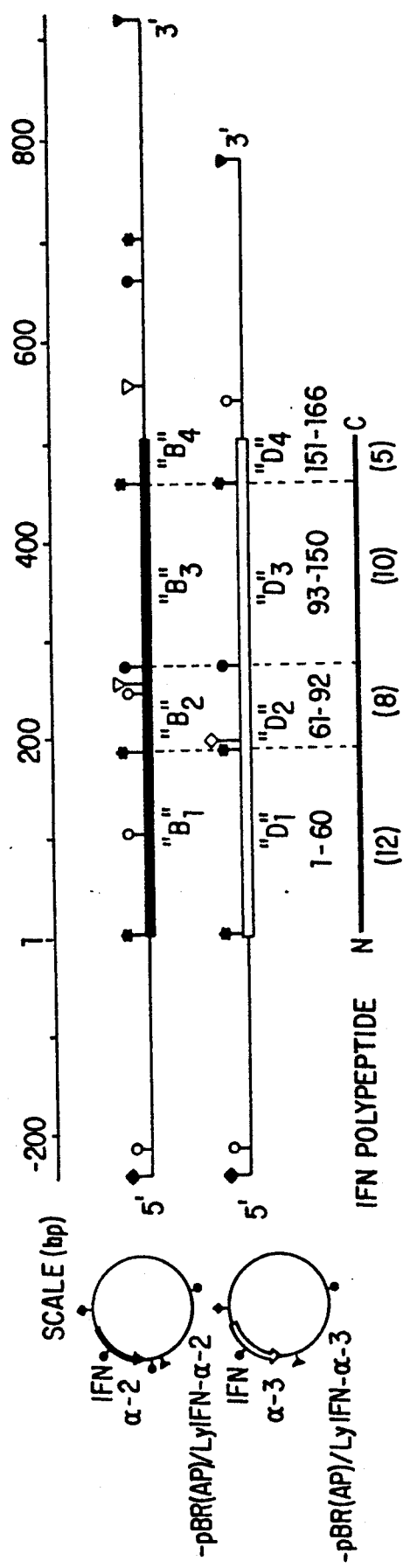
FIG. 3 shows the restriction maps of the HindIII-PstI small segments of plasmids pBR(AP)/LyIFN-α-2 and pBR(AP)/LyIFN-α-3. The white bar (LyIFN-α-3) and black bar (LyIFN-α-2) delimit the coding regions of the mature IFNs. At the bottom the subdivision of the primary structure of IFN polypeptide (166 amino acids) into four sections is shown.

1. Preparation of hybrid vectors containing a hybrid IFN structural gene

The cDNAs of human interferon-α subtypes α-2 and α-3 have been cloned in *E. coli.* Thus, plasmid pBR(AP)/LyIFN-α-2 and pBR(AP)/LyIFN-α-3 include HindIII-PstI (or EcoRI-PstI) DNA inserts containing the coding regions of LyIFN-α-2 and LyIFN-α-3 under the control of the β-lactamase promoter (cf. European Patent Application No. 76,489). The restriction maps of said inserts are depicted in FIG. 3. It can easily be seen that the genes share some common restriction sites (located at positions 60, 92 and 150 of the IFN amino acid sequences) which can be used advantageously to construct novel genes coding for hybrid interferons having favourable biological and/or physical properties.

Thus, recombinants (single or multiple exchanges) between LyIFN-α-2 and LyIFN-α-3 genes can be generated by in vitro recombination at the PvuII site (position 92) and/or at the Sau3A sites (positions 60 and 150). Since the primary structure of the interferons can thus be divided into 4 sections (first section amino acids 1 to 60, second section amino acids 61 to 92, third section amino acids 93 to 150 and fourth section amino acids 151 to 166, see FIG. 3), the hybrid interferons of the present invention can be designated by four letters each letter being indicative of the section present. Thus, for example, hybrid interferon (I) being composed of sections 1 to 3 of interferon LyIFN-α-2 ("B", LyIFN-α-2 is related to IFN-αB, supra) and section 4 of LyIFN-α-3 ("D", LyIFN-α-3 is related to IFN-αD, supra) is designated IFN "$B_1B_2B_3D_4$".

In order to facilitate the production of the desired hybrid interferon the DNA inserts containing the LyIFN-α-2 and LyIFN-α-3 coding regions, respectively, have to be modified in such a manner that for religation purposes the restriction sites HindIII (or EcoRI), PvuII and PstI are unique to them. It is evident from FIG. 3 that there is an additional PvuII site in the 3' extracistronic region of the gene coding for LyIFN-α-2. This site can easily be removed, for example by partial cleavage of a hybrid vector containing the LyIFN-α-2 coding region with PvuII, ligating the resulting linearized DNA to a linker containing a DNA sequence which is recognized by the restriction endonuclease PstI, cleaving with PstI, religating the digests at low DNA concentration and selecting for plasmids (e.g. by restriction analysis) having the desired modification, viz. a shortened 3' extracistronic region with the PvuII site eliminated. Analogously, vectors used to clone IFN genes are advantageously modified such that the restriction sites HindIII, PvuII and PstI are unique to them.

The invention relates to hybrid vectors comprising a DNA sequence which codes for any of the hybrid interferons of the formulae I–VI and is operatively linked to an expression control sequence, and to processes for the preparation thereof.

The vector is selected depending on the host cells envisaged for transformation. Examples of suitable hosts are microorganisms, which are devoid of or poor in restriction enzymes or modification enzymes, such as yeasts, for example *Saccharomyces cerevisiae*, and strains of bacteria, in particular strains of *Escherichia coli*, for example *E. coli* X1776, *E. coli* HB 101, *E. coli* W3110, *E. coli* HB101/LM1035, *E. coli* JA221 or *E. coli* K12 strain 294, Bacillus subtilis, Bacillus stearothermophilus, Pseudomonas, Haemophilus, Streptococcus and others, and furthermore cells of higher organisms, in particular established human or animal cell lines. The above strains of E. coli, for example E. coli HB101 and E. coli JA221, and furthermore Saccharomyces cerevisiae are preferred as the host microorganism.

In principle, all vectors which replicate and express the hybrid IFN genes according to the invention in the chosen host are suitable. Examples of vectors which are suitable for the expression of the hybrid interferon genes in an E. coli strain are bacteriophages, for example derivatives of λ bacteriophages, or plasmids, such as, in particular, the plasmid ColEl and its derivatives, for example pMB9, pSF2124, pBR317 or pBR322. The preferred vectors of the present invention are derived from plasmid pBR322. Suitable vectors contain a complete replicon and a marker gene, which allows to select and identify the hosts transformed with the expression plasmids on the basis of a phenotypical trait. Suitable marker genes impart to the host, for example, resistance towards heavy metals, antibiotics and the like. Furthermore, preferred vectors of the present invention contain, outside the replicon and marker gene regions, recognition sequences for restriction endonucleases, so that the hybrid IFN gene and, if appropriate, the expression control sequence can be inserted at these sites. The preferred vector, the plasmid pBR322, contains an intact replicon, marker genes which confer resistance towards tetracycline and ampicillin (tet$^R$ and amp$^R$) and a number of unique recognition sites for restriction endonucleases, for example PstI (cleaves in the amp$^R$ gene, the tet$^R$ gene remains intact), BamHI, HindIII and SalI (all cleave in the tet$^R$ gene, the amp$^R$ gene remains intact), NruI and EcoRI.

Several expression control sequences can be used for regulation of the gene expression. In particular, expression control sequences of highly expressed genes of the host to be transformed are used. In the case of pBR322 as the hybrid vector and E. coli as the host microorganism, for example, the expression control sequences (which contain, inter alia, the promoter and the ribosomal binding site) of the lactose operon, tryptophan operon, arabinose operon and the like, the β-lactamase gene, the corresponding sequences of the phage λN gene or the phage fd-coat protein gene and others, are suitable. Whilst the plasmid pBR322 already contains the promoter of the β-lactamase gene (β-lac gene), the other expression control sequences must be introduced into the plasmid.

Vectors which are suitable for replication and expression in yeast contain a yeast replication start and a selective genetic marker for yeast. Hybrid vectors which contain a yeast replication start, for example chromosomal autonomously replicating segment (ars), are retained extrachromosomally within the yeast cell after the transformation and are replicated autonomously. Furthermore, hybrid vectors which contain sequences homologous to the yeast 2μ plasmid DNA can be used. Such hybrid vectors will get integrated by recombination into 2μ plasmids already existing within the cell, or replicate autonomously. 2μ sequences are particularly suitable for plasmids with a high transformation frequency and permit high copy numbers. The preferred yeast vector of the present invention is the plasmid pJDB207.

Suitable marker genes for yeasts are, in particular, those which impart antibiotic resistance to the host or, in the case of auxotrophic yeast mutants, genes which complement host lesions. Corresponding genes impart, for example, resistance towards the antibiotic cycloheximide or provide for protrophy in an auxotrophic yeast mutant, for example the URA3, LEU2, HIS3 or, in particular, TRP1 gene. Yeast hybrid vectors furthermore preferably contain a replication start and a marker gene for a bacterial host, in particular E. coli, so that the construction and cloning of the hybrid vectors and their intermediates can take place in a bacterial host.

Expression control sequences which are suitable for expression in yeast are, for example, those of highly expressed yeast genes. Thus, the promoters of the TRP1 gene, the ADHI or ADHII gene, acid phosphatase (PHO3 or PHO5) gene, isocytochrome gene or a promoter involved with the glycolytic pathway, such as the promoter of the enolase, glyceraldehyde-3-phosphate dehydrogenase (GAPDH), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, can be used. Preferred vectors of the present invention contain promoters with transcriptional control, e.g. the promoters of the PHO5, ADH II and GAPDH genes, which can be turned on or off by variation of the growth conditions. For example, the PHO5 promoter can be repressed or derepressed solely by increasing or decreasing the concentration of inorganic phosphate in the medium.

Promoters for use in mammalian cells are for example viral promoters, such as HTLV, SV40, vaccinia promoter and the like.

The promoter is operatively linked to the coding region so as to ensure effective expression of the hybrid interferon. In one embodiment of the present invention, the promoter is directly linked to the coding region of mature hybrid IFN with a translation start signal (ATG) inserted at the junction. A preferred region for joining the promoter to the hybrid IFN coding region is between the major mRNA start and the ATG of the gene naturally attached to said promoter.

In another embodiment of the present invention, especially if yeast is used as the host microorganism, a signal sequence is included in the construction. Suitable signal sequences are those naturally linked to the promoter used. For example the PHO5 signal sequence, furthermore the signal sequences of the yeast invertase or α-factor genes may be used. Those combinations are favoured which allow a precise cleavage between the signal sequence and the mature hybrid IFN amino acid sequence. Additional sequences, such as pro- or spacer-sequences which may or may not carry specific processing signals can also be included in the constructions to facilitate accurate processing of precursor molecules. Alternatively fused proteins can be generated containing internal processing signals which allow proper maturation in vivo or in vitro.

Preferably, the hybrid vectors according to the present invention comprise also the 3'-flanking sequence of a gene which contains the proper signals for transcription termination and polyadenylation. Suitable 3'-flanking sequences are for example those of the gene naturally linked to the promoter used. In the case yeast is used as the host microorganism and the PHO5 promoter is used as expression control sequence, the 3'-flanking sequence is preferably that of the PHO5 gene.

In a preferred embodiment, the present invention relates to hybrid vectors capable of replication and phenotypical selection in a host strain comprising a promoter and a DNA sequence encoding any of the novel hybrid interferons, said DNA sequence being positioned together with transcription start and termination signals as well as translation start and stop signals in said hybrid vectors under the control of said promoter such that in a transformed host it is expressed to produce a hybrid interferon according to the invention.

The hybrid vectors according to the present invention can be produced by in vitro ligation of appropriate segments of the LyIFN-$\alpha$-2 and LyIFN-$\alpha$-3 coding regions and inserting the resulting hybrid IFN gene into a suitable vector or by ligating a particular IFN DNA segment to a linearized vector DNA already containing the remaining sections in such a way that the gene coding for the desired hybrid interferon is formed. It is preferred that the DNA segment donating the amino terminal end sequence is already fused to the expression control sequence.

Appropriate segments of the LyIFN-$\alpha$-2 and LyIFN-$\alpha$-3 coding regions are especially taken from the preferred starting vectors of the present invention, viz. the pBR322 derived plasmids pAM2 and pAM21. The plasmid pAM2 contains a HindIII-PstI insert with the LyIFN-$\alpha$-3 coding region under the control of the $\beta$-lactamase promoter. The vector part of plasmid pAM2 is resistant to PvuII. The plasmid pAM21 contains a HindIII-PstI insert with the LyIFN-$\alpha$-2 coding region having a unique PvuII site at position 92 and being under the control of the $\beta$-lactamase promoter. The vector part of plasmid p21 is likewise resistant to PvuII.

Especially, the gene coding for hybrid interferon "$B_1B_2B_3D_4$" is prepared by ligating the large PstI-PvuII fragment of plasmid pAM21, the small Sau3A-PvuII fragment of plasmid pAM21 and the small Sau3A-PstI fragment of plasmid pAM2. This construction results in a plasmid (pJC344) containing the hybrid interferon "$B_1B_2D_3B_4$" coding region under the control of the $\beta$-lactamase promoter. In a similar manner, the gene coding for hybrid interferon "$B_1B_2D_3B_4$" is prepared by ligating the large PvuII-PstI fragment of plasmid pAM21, the small Sau3A-PvuII fragment of plasmid pAM2 and the small Sau3A-PstI fragment of plasmid pAM21. This construction results in a plasmid (pJC342) containing the hybrid interferon "$B_1B_2D_3B_4$" coding region under the control of the $\beta$-lactamase promoter. The gene coding for hybrid interferon "$B_1D_2D_3D_4$" can be prepared by ligating the small HindIII-Sau3A fragment of plasmid pAM21, the small Sau3A-PvuII fragment of plasmid pAM2 and the large PvuII-HindIII fragment of plasmid pAM2. This construction results in a plasmid (pAM94) containing the hybrid interferon "$B_1D_2D_3D_4$" coding region under the control of the $\beta$-lactamase promoter. Analogously, the gene coding for hybrid interferon "$B_1D_2B_3B_4$" is prepared by ligating the small HindIII-Sau3A fragment of plasmid pAM21, the small Sau3A-PvuII fragment of plasmid pAM2 and the large PvuII-HindIII fragment of plasmid pAM21. This construction results in a plasmid (pAM90) containing the hybrid interferon "$B_1D_2B_3B_4$" coding region under the control of the $\beta$-lactamase promoter. Plasmids containing the hybrid interferon "$B_1D_2B_3D_4$" coding region (e.g. plasmid pDM1) or the hybrid interferon "$B_1D_2D_3B_4$" coding region (e.g. plasmid pDM2) may be prepared in a similar manner. These plasmids are suitable for replicating and expressing the hybrid IFN genes in *E. coli*. If desired, the DNA insert coding for any of said hybrid interferons may be excised from the corresponding plasmid and introduced into a different vector DNA. In this manner, plasmids may be obtained which contain the hybrid interferon coding region under the control of a promoter other than the $\beta$-lactamase promoter and/or allow the gene to be expressed in a host different from *E. coli*.

The preparation of DNA comprising the structural gene for any of said hybrid interferons may also be performed by means of chemical synthesis. Suitable methods for the synthesis of DNA have been presented in summary form by S. A. Narang, [Tetrahedron 39, 3 (1983)]. The known synthesis techniques allow the preparation of polynucleotides towards 20 bases in length, in good yield, high purity and in a relatively short time. Suitably protected nucleotides are linked with one another by the phosphodiester method [K. L. Agarwal et al., Angew. Chem. 84, 489 (1972)], or the even more efficient phosphotriester method [C. B. Reese, Tetrahedron 34, 3143 (1972)] or phosphite triester method [R. L. Letsinger et al., J. Am. Chem. Soc. 98, 3655 (1976)]. Simplification of the synthesis of the oligonucleotides and polynucleotides is made possible by the solid phase method, in which the nucleotide chains are bound to a suitable polymer. Itakura et al. [J. Am. Chem. Soc. 103, 706 (1981)] use trinucleotides linked by the phosphotriester method in the solid phase synthesis, instead of individual nucleotides, and these can thus be condensed, in a short time and with good yields, for example, to give a polynucleotide with 31 bases. The actual double-stranded DNA can be built up enzymatically from chemically prepared short segments. For this, Khorana et al. [J. Biol. Chem. 251, 565 (1976)] use overlapping polynucleotide sequences from both DNA strands, which are held together in the correct arrangement by base-pairing and are then chemically linked by the enzyme DNA ligase. Another possibility comprises incubating in each case one polynucleotide sequence from the two DNA strands with a short overlapping segment in the presence of the four required deoxynucleoside triphosphates with a DNA-polymerase, for example DNA-polymerase I, a Klenow fragment of polymerase I or T$_4$ DNA polymerase, or with AMV (avian myeloblastosis virus) reverse transcriptase. The two polynucleotide sequences are thereby held together in the correct arrangement by base-pairing and are supplemented with the required nucleotides by the enzyme to give a complete double-stranded DNA [S. A. Narang et al., Anal. Biochem. 121, 356 (1982)]. Itakura et al. [J. Biol. Chem. 257, 9226 (1982)] describe how, on the basis of this principle, a segment 132 base pairs long of the human leukocyte interferon $\alpha_2$-gene can be built in the presence of DNA-polymerase I (Klenow fragment) from 4 chemically synthesised fragments 39 to 42 bases in length, a 40% saving in chemical synthesis in comparison with the method which uses only ligase being achieved. A suitable procedure for preparing the DNAs according to the present invention has been described, for example, in European Patent Application No. 146,785 the teaching of which is herein incorporated by reference.

The chemically synthesized DNA comprising the structural gene for any of the hybrid interferons according to the invention may be inserted into a vector DNA containing an expression control sequence in a manner such that the expression control sequence regulates the expression of said gene.

2. Transformation of the host cells

The invention also relates to a process for the preparation of a transformed host, which comprises transforming a host with an expression vector containing a DNA sequence which codes for any of the hybrid interferons according to the invention and is regulated by an expression control sequence.

Examples of suitable hosts are the above-mentioned microorganisms, such as strains of *Saccharomyces cerevisiae, Bacillus subtilis* and *Escherichia coli*. The transformation with the expression plasmids according to the invention is carried out, for example, as described in the literature, thus for *S. cerevisiae* [A. Hinnen et al., Proc. Natl. Acad. Sci. USA 75, 1929 (1978)], *B. subtilis* [Anagnostopoulos et al., J. Bacteriol. 81, 741 (1961)] and *E. coli* [M. Mandel et al., J. Mol. Biol. 53, 159 (1970)].

Accordingly, the transformation procedure of *E. coli* cells includes $Ca^{2+}$-pretreatment of the cells so as to allow DNA uptake, and incubation with the hybrid vector. The cells are transferred to a selective growth medium which allows separation of the transformed cells from the parent cells. Cells which do not contain the vector will not survive in such a medium. The transformation of yeast comprises, for example, the steps of (1) enzymatic removal of the yeast cell wall by means of glucosidases, (2) treatment of the obtained spheroplasts with the vector in the presence of polyethyleneglycol and $Ca^{2+}$-ions and (3) regeneration of the cell wall by embedding the spheroplasts into agar. Preferably, the regeneration agar is prepared in a way to allow regeneration and selection of the transformed cells at the same time.

The invention relates also to the transformed hosts obtainable by the route described.

3. Cultivation of the transformed host cells and isolation of the expressed hybrid interferon The invention concerns further a method for the preparation of the hybrid interferons of the formulae I-VI, characterized in that host cells transformed with a hybrid vector which contains a DNA sequence coding for any of said hybrid interferons are cultured, and the hybrid interferon is isolated.

The transformed host cells are cultured by methods known in the art in a liquid medium containing assimilable sources of carbon, nitrogen and inorganic salts.

Various sources of carbon can be used for culture of the transformed hosts according to the invention. Examples of preferred sources of carbon are assimilatable carbohydrates, such as glucose, maltose, mannitol or lactose, or an acetate, which can be used either by itself or in suitable mixtures. Examples of suitable sources of nitrogen are amino acids, such as casaminoacids, peptides and proteins and their degradation products, such as tryptone, peptone or meat extracts; and furthermore yeast extracts, malt extract and also ammonium salts, for example ammonium chloride, sulfate or nitrate, which can be used either by themselves or in suitable mixtures. Inorganic salts which can also be used are, for example, sulfates, chlorides, phosphates and carbonates of sodium, potassium, magnesium and calcium.

The medium furthermore contains, for example, growth-promoting substances, such as trace elements, for example iron, zinc, manganese and the like, and preferably substances which exert a selection pressure and prevent the growth of cells which have lost the expression plasmid. Thus, for example, ampicillin is added to the medium if the expression plasmid contains an $amp^R$ gene. Such an addition of antibiotic substances also has the effect that contaminating antibiotic-sensitive microorganisms are destroyed. If a yeast strain which is auxotrophic in, for example, an essential amino acid, is used as the host microorganism the plasmid preferably contain a gene coding for an enzyme which complement the host defect. Cultivation of the yeast strain is performed in a minimal medium deficient in said amino acid.

Culture is effected by processes which are known in the art. The culture conditions, such as temperature, pH value of the medium and fermentation time, are chosen so that a maximum titre of hybrid interferon is obtained. Thus, an *E. coli* or yeast strain is preferably cultured under aerobic conditions by submerged culture with shaking or stirring at a temperature of about 20° to 40° C., preferably about 30° C., and a pH value of 4 to 8, preferably at about pH 7, for about 4 to 30 hours, preferably until maximum yields of the hybrid interferon are reached.

It is surprisingly found that the maximum titres of the hybrid interferons according to the invention, for example of hybrid interferons "$B_1D_2D_3B_4$", "$B_1D_2B_3D_4$", "$B_1D_2D_3D_4$" and "$B_1D_2B_3B_4$", attainable in crude extracts of, for example, transformed yeast cultured under standard conditions are distinctly higher than those of interferon-α-2 and hybrid interferons "$B_1B_2D_3D_4$" and "$D_1D_2B_3B_4$" which are closely related to hybrid interferons "BD" and "DB" described in U.S. Pat. No. 4,414,150.

When the cell density has reached a sufficient value, the culture is interrupted and the hybrid interferon is released from the cells of the host. For this purpose, the cells are destroyed, for example by treatment with a detergent, such as SDS or triton, or lysed with lysozyme or a similarly acting enzyme. If yeast is used as host microorganism the cell wall may be removed by enzymatic digestion with a glucosidase. Alternatively or additionally, mechanical forces, such as shearing forces (for example X-press, French press, Dyno mill) or shaking with glass beads or aluminium oxide, or alternating freezing, for example in liquid nitrogen, and thawing, for example to 30° to 40° C., as well as ultrasound can be used to break the cells. The resulting mixture, which contains proteins, nucleic acids and other cell constituents, is enriched in proteins, including hybrid interferon, in a manner which is known per se, after centrifugation. Thus, for example, most of the non-protein constituents are removed by polyethyleneimine treatment and the proteins, including hybrid interferon, are precipitated, for example, by saturation of the solution with ammonium sulfate or with other salts. Bacterial proteins can also be precipitated by acidification with acetic acid (for example 0.1%, pH 4-5). Further purification steps include, for example, ultrafiltration, diafiltration, gel electrophoresis, chromatographic processes, such as ion exchange chromatography, size exclusion chromatography, HPLC, reverse phase HPLC and the like, separation of the constituents of the mixture according to molecular size by means of a suitable Sephadex column, dialysis, affinity chromatography, for example antibody, especially monoclonal antibody, affinity chromatography, and other known processes, especially those known in the art.

Surprisingly, the hybrid interferons according to the invention have higher thermstabilities than interferon LyIFN-α-2 and hybrid interferon "$B_1B_2D_3D_4$". Thus, the temperature at which 50% of the antiviral activity is lost (temperature increase of IFN solutions at 1°

C./min) is 62.8° C. in the case of LyIFN-α-2 and 63° C. in the case of hybrid interferon "$B_1B_2D_3D_4$" whereas the corresponding values of, for example, hybrid interferons "$B_1D_2D_3D_4$", "$B_1D_2B_3B_4$", "$B_1D_2B_3D_4$" and "$B_1D_2D_3B_4$" are 65° C., 64.7° C., 65.3° C. and 64.2° C., respectively.

The invention concerns furthermore the hybrid interferons of the formulae I–VI whenever prepared according to the methods of the present invention.

The invention concerns also the hybrid interferons obtainable according to the inventive process.

The invention concerns especially the hybrid vectors, the transformed host cells, the hybrid interferon polypeptides and the processes for the preparation thereof as described in the Examples.

BIOLOGICAL PROPERTIES OF THE HYBRID INTERFERONS AND PHARMACEUTICAL FORMULATIONS

The hybrid interferons according to the present invention exhibit interesting biological properties which qualify them as valuable pharmaceuticals.

The hybrid interferons of the invention are distinguished by a very potent antiviral activity on mammalian cells, such as bovine and especially human cells. Thus, the antiviral titres determined as the reduction of cytopathic effect according to the method of S. Rubinstein et al. [J. Virol. 37, 755 (1981) using vesicular stomatitis virus (VSV) as the challenge virus on bovine (MDBK) and human (WISH) cells] are as follows:

TABLE 1

Antiviral titres of hybrid interferons using VSV as challenge virus

| interferon | specific activity/mg protein bovine | human |
|---|---|---|
| "$B_1D_2D_3D_4$" | $1.25 \cdot 10^8$ | $1.3 \cdot 10^8$ |
| "$B_1D_2B_3B_4$" | $1.25 \cdot 10^8$ | $1.3 \cdot 10^8$ |
| "$B_1B_2B_3B_4$" | $9.5 \cdot 10^7$ | $>2 \cdot 10^8$ |
| "$B_1D_2B_3D_4$" | $1.9 \cdot 10^8$ | $7.7 \cdot 10^7$ |
| "$B_1D_2D_3B_4$" | $7.2 \cdot 10^7$ | $3.8 \cdot 10^7$ |
| "$B_1B_2B_3D_4$" | $1.05 \cdot 10^8$ | $8 \cdot 10^7$ |
| "$D_1D_2B_3B_4$" (DB) | $8.5 \cdot 10^7$ | $3.3 \cdot 10^5$ |
| "$B_1B_2D_3D_4$" (BD) | $1.15 \cdot 10^8$ | $2.33 \cdot 10^8$ |
| α-2 ("B") | $1.05 \cdot 10^8$ | $2.13 \cdot 10^8$ |
| α-3 ("D") | $5.5 \cdot 10^7$ | $6.7 \cdot 10^6$ |

Accordingly, the antiviral action of the hybrid interferons according to the invention is not confined to human cells but is invariably interspecific. Thus, the antiviral activities of hybrid interferons "$B_1D_2D_3D_4$", "$B_1D_2B_3B_4$", "$B_1B_2B_3B_4$", "$B_1D_2B_3D_4$" and "$B_1B_2B_3D_4$" exhibited on human cells are comparable in degree to those of parent interferon α-2 and hybrid interferon "$B_1B_2D_3D_4$" which is closely related to hybrid interferon "BD" disclosed in U.S. Pat. No. 4,414,150, but are distinctly superior to parent interferon α-3 (by factor 10–30) and to reference hybrid interferon "$D_1D_2B_3B_4$" (by factor 230–600).

Apart from the general antiviral activity on human cells, the hybrid interferons according to the invention give rise to a more specific response of target cells. Thus, various intracellular enzymes are induced on interferon action. Among these enzymes is (2'-5') oligoisoadenylate synthetase ("2–5 A synthetase") whichs generates (2'5') linked oligonucleotides, and these in turn activate a latent endoribonuclease which cleaves viral mRNA. It is surprisingly found that the hybrid interferons according to the invention, such as "$B_1D_2D_3D_4$", "$B_1D_2B_3B_4$", "$B_1B_2B_3B_4$" and "$B_1B_2D_3B_4$", are particularly active inducers of 2–5 A synthetase activity in human cells. Thus, at $10^3$ units/ml hybrid interferons "$B_1D_2D_3D_4$", "$B_1D_2B_3B_4$", "$B_1B_2B_3D_4$" and "$B_1B_2D_3B_4$ give a 17.5 fold, 11.4 fold, 8.5 fold and 9.6 fold increase, respectively, in 2–5 A synthetase activity in Daudi cells compared to a 5.6, 3.9, 4.0 or 4.3 fold increase on action of parent interferons α-2 and α-3 and reference hybrid interferons "$B_1B_2D_3D_4$" and "$D_1D_2B_3B_4$", respectively.

Furthermore, the hybrid interferons according to the present invention show antiproliferative activities. The antiproliferative activity can be assayed as follows: interferon containing solutions are incubated with $5 \cdot 10^4$ Daudi cells per ml in 2 ml RPMI medium containing 10% foetal calf serum. Cells multiplication is determined after 3 days incubation by counting viable cells in an haemocytometer using the Trypan blue exclusion test. Thus, the concentration of hybrid interferon "$B_1D_2D_3D_4$", "$B_1D_2B_3B_4$", "$B_1B_2B_3D_4$", "$B_1B_2D_3D_4$", "$B_1D_2B_3D_4$" and "$B_1D_2D_3B_4$" required to induce a 50% inhibition of Daudi cell multiplication is about 4, 4, 1.3, 1.3, 4 and 4 units/ml, respectively, hence approximately equivalent to parent interferon α-2 and reference hybrid interferon "$B_1B_2D_3D_4$" (about 1.3 units/ml) and superior to parent interferon α-3 (about 20 units/ml) and reference hybrid interferon "$D_1D_2B_3B_4$" (about 400 units/ml).

The antiproliferative activity against human cancers can also be demonstrated in vivo. Thus, various cancers of human origin, such as cancers of the breast, colon and lung, ovarian cancer and melanoma, have been propagated in nude mice. Small fragments of the propagated tumors are isolated and implanted by trochar under the venal capsule of (Balb/c×DBA/2)F$_1$ (CDF$_1$) mice. IFN is administered intramuscularly at two daily doses of from $5 \cdot 10^6$ to $5 \cdot 10^7$ IU/kg/inj. at days 1 to 5 (day of administration: day 0). At day 6 the animals are sacrificed, the final tumor sizes are measured and compared to the initial tumor sizes (before IFN treatment) and to the tumor sizes in untreated control mice. Upon treatment with the hybrid interferons according to the invention, for example "$B_1D_2D_3D_4$" and "$B_1B_2B_3B_4$", a considerable and significant inhibition of tumor growth and, partially, regression of tumors is observed. Surprisingly, the antiproliferative activity of the hybrid interferons is superior to that of parental interferons α-2 and α-3 as well as to that of hybrid interferons "$B_1B_2D_3D_4$" and "$D_1D_2B_3B_4$".

The antiviral and antiproliferative properties of the hybrid interferons according to the invention make these polypeptides useful for treating viral infections, such as influenza and other respiratory tract virus infections, herpes virus infections, rabies and hepatitis infection, and neoplastic diseases, such as melanoma, renal cancer and hairy cell leukemia, of the human or animal body, optionally in combination with other antiviral or antitumor agents, preferably in the form of pharmaceutical preparations that contain a therapeutically effective amount of the active ingredient optionally together or in admixture with inorganic or organic, solid or liquid, pharmaceutically acceptable carriers which are suitable preferably for parenteral administration.

Parenteral formulations are especially injectable fluids that are effective in various manners, such as intravenously, intramuscularly, intraperitoneally, intranasally, intradermally or subcutaneously. Such fluids are preferably isotonic aqueous solutions or suspensions which can be prepared before use, for example from lyophilised preparations which contain the active ingredient alone or together with a pharmaceutically acceptable carrier. The pharmaceutical preparations may be sterilised and/or contain adjuncts, for example preservatives, stabilisers, wetting agents and/or emulsifiers, solubilisers, salts for regulating the osmotic pressure and/or buffers. The present pharmaceutical preparations, which may, if desired, contain further pharmacologically valuable substances, are produced in a manner known per se, for example by means of conventional dissolving of lyophilising processes, and contain from approximately 0.1% to 100%, especially from approximately 1% to approximately 50%, and in the case of lyophilisates up to 100%, of the active ingredient. It is worthy of note that the hybrid interferons according to the invention, such as "$B_1D_2D_3D_4$", can be lyophilised and redissolved without any loss of activity. In contrast thereto, lyophilised preparations of parental interferons $\alpha$-2 and $\alpha$-3 give turbid solutions with a remarkable decrease in activity. The latter interferons can therefore only be stored in buffered solutions.

The invention also concerns a method for producing a pharmaceutical composition characterized in that a pharmacologically active compound of the present invention is admixed with a pharmaceutically acceptable carrier.

The particular mode of administration and the dosage will be selected by the attending physician taking into account the particulars of the patient, the disease and the disease state involved. For instance, viral infections are usually treated by daily or twice daily doses over a few days to a few weeks whereas treatment of neoplasms typically involves daily or multidaily doses over weeks or months. The same daily dose levels, viz. about $10^6$ to $10^7$ units, as are used in conventional interferon therapy may be applied.

MONOCLONAL ANTIBODY TO THE INTERFERON HYBRIDS

It is an object of the invention to provide a novel monoclonal antibody to IFN$\alpha$ with high affinity for several subtypes of IFN$\alpha$ including IFN$\alpha$ hybrids and low affinity for other subtypes of IFN$\alpha$, and hybridoma cells secreting them.

The novel monoclonal antibody is characterized in that it has a high affinity towards IFN$\alpha$/B, D, F and related subtypes [cf. D. V. Goeddel et al., Nature 290, 20 (1981)] as well as hybrids of these subtypes, especially the hybrid interferons according to the invention, but low affinity towards, for example, IFN$\alpha$/A subtype.

The monoclonal antibody is designated 144 BS. This monoclonal antibody is secreted by the hybridoma cell line with the designation 144 BS 22-6-19. The invention concerns also derivatives of this monoclonal antibody, e.g. antibody fragments, radioactively labelled monoclonal antibodies, and conjugates of the monoclonal antibody with enzymes or the like.

Fragments of the monoclonal antibody of this invention are e.g. Fab, Fab' or F(ab')$_2$ fragments, which retain their specificity for the antigenic determinants, i.e. which retain the characteristic binding pattern of the parent monoclonal antibody to human IFN$\alpha$ and IFN$\alpha$ hybrid subtypes.

Radioactively labelled monoclonal antibodies contain e.g. radioactive iodine ($^{123}$I, $^{125}$I, $^{131}$I), carbon ($^{14}$C), sulfur ($^{35}$S), tritium ($^3$H) or the like. Preferred are monoclonal antibodies labelled with radioactive iodine.

Antibody conjugates of the invention are e.g. conjugates of the monoclonal antibody or fragments thereof with enzymes such as horseradish peroxidase, alkaline phosphatase, $\beta$-D-galactosidase, glucoseoxidase, glucoamylase, carboanhydrase, acetylcholinesterase, lysozyme, malate dehydrogenase or glucose-6-phosphate dehydrogenase, or with avidin or biotin. In such conjugates the antibody is bound to the enzymes directly or by the way of a spacer or linker group. Preferred are conjugates of the monoclonal antibody with the enzymes horseradish peroxidase or alkaline phosphatase.

The monoclonal antibody of the invention is characterized by its binding ability towards polypeptides belonging to different subtypes of human IFN$\alpha$. The binding ability is determined e.g. in the so-called combined immunoprecipitation bioassay as described by S. S. Alkan et al. in "Protides of the biological fluids", Ed. H. Peeters, Pergamon Press, Vol. 30, pages 495–498 (1983). In this assay, an IFN$\alpha$ containing solution is incubated with the monoclonal antibody to be tested, the bound and unbound monoclonal antibodies precipitated by the addition of a polyclonal serum binding all the antibodies tested, the immune precipitate separated and redissolved in acid solution, and the IFN$\alpha$ liberated thereby determined in a classical bio-assay based on the antiviral activity of IFN$\alpha$.

It is surprising that the monoclonal antibody of the invention binds strongly to IFN$\alpha$ subtypes B, D, F and to hybrids thereof, also IFN$\alpha$ subtypes C and J, but display low affinity towards IFN$\alpha$ subtype A, a subtype which is bound by all other known monoclonal antibodies recognizing more than three IFN$\alpha$ subtypes, i.e. antibodies with broad subtype recognition such as the monoclonal antibody NK2 [D. Secher et al., Nature 285, 446 (1980)], the monoclonal antibodies EBI-1, 2 and 3 disclosed in the European Patent Application EP 119,476 or the monoclonal antibody LO-22 disclosed in the Patent Application WO 84/03106.

Compared with the monoclonal antibody YOK disclosed in Patent Application WO 84/03105, which is specific for IFN$\alpha$ subtype D, the monoclonal antibody of the invention surprisingly show broad specificity, particularly towards IFN$\alpha$ subtypes B and F not bound by the antibody YOK.

The monoclonal antibody of the invention with the designation 144 BS is found to belong to the immunoglobulin class IgG$_1$½ (Kappa) as determined by well-known methods, e.g. the immuno diffusion Ouchterlony technique using class-specific second antibodies.

The monoclonal antibody of the invention and derivatives thereof are obtained by processes known per se, characterized in that the hybridoma cell line 144 BS 22-6-19 a) is cultivated in vitro and the monoclonal antibody isolated from the culture supernatant, or
b) is propagated in vivo in a suitable mammal and the monoclonal antibody recovered from body fluids of said mammal, and, if desired
c) the obtained monoclonal antibody is converted into a derivative thereof.

Suitable culture media for the in vitro cultivation according to process a) are standard culture media such as Dulbecco's Modified Eagle Medium or RPMI 1640 Medium, optionally replenished by a mammal serum, e.g. fetal calf serum. The isolation of the monoclonal antibody is accomplished by precipitating the protein contained in the culture supernatants by ammonium sulfate or the like, followed by purifying the immunoglobulin by standard chromatographic methods, such as gel filtration, ion exchange chromatography, chromatography on DEAE cellulose, or immunoaffinity chromatography.

Large amounts of the desired monoclonal antibody can be obtained by the propagation of the hybridoma cell line according to process b). Cell clones are injected into syngeneic mammals, which causes antibody-producing tumours to grow. After one to three weeks the desired monoclonal antibody is recovered from body fluids of said mammal. As an example the hybridoma cell line which is derived from Balb/c mice is intraperitoneally injected into Balb/c mice optionally pretreated with a hydrocarbon such as pristane, and after one to two weeks, ascites fluid of these mice is collected. The monoclonal antibody is isolated from the body fluids by methods known per se, e.g. by precipitating the protein with ammonium sulfate or the like, followed by purifying the immunoglobulin by standard chromatographic methods, such as gel filtration, ion exchange chromatography, chromatography on DEAE cellulose, or immunoaffinity chromatography.

Fragments of the monoclonal antibody, for example Fab, Fab' or F(ab')$_2$ fragments, which retain their specificity towards the antigenic determinants of the IFN$\alpha$ subtypes, can be obtained from the monoclonal antibody prepared according to process a) or b) by methods known per se, e.g. by digestion with enzymes such as pepsin or papain and/or cleavage of disulfide bonds by chemical reduction. Monoclonal antibodies labelled with radioactive iodine are prepared by iodination methods known in the art, e.g. by labelling the monoclonal antibody with radioactive sodium or potassium iodide and a chemical oxidant such as sodium hypochlorite, chloramine T or the like, or an enzymatic oxidant such as lactoperoxidase, glucose oxidase and glucose. Radioactively labelled monoclonal antibodies of the invention are also prepared by adding radioactively labelled nutrients to the culture media of the in vitro cultivation of step a). Such labelled nutrients contain e.g. radioactive carbon ($^{14}$C), tritium ($^3$H), sulfur ($^{35}$S) or the like, and are for example L-($^{14}$C)-leucine, L-($^3$H)-leucine or L-($^{35}$S)-methionine.

Conjugates of the monoclonal antibody of the invention are prepared by methods known in the art, e.g. by reacting the monoclonal antibody prepared according to process a) or b) or a fragment thereof prepared as described hereinbefore with an enzyme in the presence of a coupling agent, e.g. glutaraldehyde, periodate, N,N'-o-phenylenedimaleimide, N-(m-maleimidobenzoyloxy)-succinimide, N-(3-(2'-pyridyldithio)-propionoxy)-succinimide, N-ethyl-N'-(3-dimethylaminopropyl)-carbodiimide or the like. Conjugates with avidin are prepared likewise. Conjugates with biotin are prepared e.g. by reacting the monoclonal antibody with an activated ester of biotin such as the biotin N-hydroxysuccinimide ester.

The invention further relates to the hybridoma cell line with the designation 144 BS 22-6-19, which has been deposited on Mar. 14, 1985 at the "Collection Nationale de Cultures de Microorganismes", Institut Pasteur, Paris, under the number I-424. This hybridoma cell line is a hybrid of the mouse myeloma cell line Sp2/O-Ag14 and of a B lymphocyte of the spleen of a Balb/c mouse immunized with natural human IFN$\alpha$. It is a stable cell line, which secretes the monoclonal antibody with the designation 144 BS. The cell line may be kept in culture or deep-frozen in liquid nitrogen and reactivated by thawing.

The invention relates also to a process for the production of said hybridoma cell line secreting the monoclonal antibody 144 BS, characterized in that Balb/c mice are immunized with a natural human IFN$\alpha$, antibody-producing spleen cells of the mice are fused with cells of the myeloma cell line Sp2/O-Ag14, the hybrid cells obtained in the fusion are cloned, and a cell clone secreting the desired antibody is selected.

The immunization of the mice is performed e.g. by injecting natural human IFN$\alpha$ two to four times parenterally, such as intraperitoneally and/or subcutaneously, at intervals of 10 to 40 days, in amounts of about $10^5$ IU to about $10^6$ IU. The injections optionally contain an adjuvant stimulating the lymphocyte production such as complete or incomplete Freund's adjuvant.

Antibody-producing spleen cells, taken two to five days after the final booster injection, are fused with cells of the myeloma cell line Sp2/O-Ag14 in the presence of a fusion promoter. Fusion promoters considered are e.g. Sendai virus or other paramyxo viruses, optionally in UV-inactivated form, calcium ions, surface-active lipids such as lysolecithin, or polyethylene glycol. Preferentially, the myeloma cells are fused with a three- to twentyfold excess of spleen cells from immunized mice in a solution containing about 30% to about 60% polyethylene glycol of a molecular weight between 1000 and 4000.

After the fusion, the cells are resuspended and cultivated in selective HAT medium. Thereby, only hybridoma cells will survive, because they combine the ability to grow and replicate in vitro, which ability is inherited from the myeloma cells, with the missing HGPRT or TK genes essential for the survival in the HAT medium, which genes are inherited from the antibody-producing spleen cells of the immunized mice.

Suitable culture media for the expansion of hybridoma cells are the standard culture media, such as Dulbecco's Modified Eagle Medium, minimum essential medium, RPMI 1640 medium and the like, optionally replenished by serum, e.g. 10 to 15% fetal calf serum. Preferentially feeder cells are added at the beginning of the cell growth, e.g. normal mouse peritoneal exsudate cells, spleen cells, marrow bone macrophages, or the like. The culture media are supplemented with selective HAT medium at regular interval in order to prevent normal myeloma cells overgrowing the hybridoma cells.

The hybridoma cell culture supernatants are screened for the desired monoclonal antibody, preferentially with a combined immunoprecipitation-bioassay or a radioimmunoassay. Positive hybridoma cells are cloned, e.g. by limiting dilution, preferentially twice or more. The cloned cell lines may be frozen in a conventional manner.

The monoclonal antibody of the invention and/or its derivatives are useful for the qualitative and quantitative determination and/or purification of human IFN$\alpha$ subtypes of natural sources or prepared by recombinant DNA methods and of human hybrid IFNs, especially those according to the present ivention.

For instance, the monoclonal antibody or derivative thereof, such as an enzyme conjugate or a radioactive derivative, can be used in any of the known immunoassays, which rely on the binding interaction between the antigenic determinant, e.g. of a polypeptide with IFNα activity, and the monoclonal antibody. Examples of such assays are radioimmunoassays, enzyme immunoassays, immunofluorescence, latex agglutination, and hemagglutination. Such immunoassays are useful e.g. in the monitoring of the production and purification of IFNα from natural sources or genetically engineered microorganisms and of hybrid IFNα proteins and in the qualitative and quantitative determination of IFNα and hybrid IFNα in biological fluids, e.g. of patients under IFNα therapy or in need of such therapy.

The monoclonal antibody according to the invention can be used as such or in the form of a radioactively labelled derivative in a radioimmunoassay (RIA). Any of the known modifications of an RIA can be used, for example RIA in homogeneous phase, solid phase RIA or heterogeneous RIA, single RIA or double (sandwich) RIA with direct or indirect (competitive) determination of IFNα. There is preferred a sandwich RIA in which a suitable carrier, for example the plastics surface of a microtitre plate or of a test tube, for example of polystyrene, polypropylene or polyvinyl chloride, glass or plastics beads, filter paper, or dextran, cellulose acetate or nitrocellulose sheets or the like, is coated with a monoclonal antibody specific for an IFNα subtype by simple adsorption or optionally after activation of the carrier, for example with glutaraldehyde or cyanogen bromide, and incubated with the test solution and a solution of a monoclonal antibody radioactively labelled with $^{125}I$, the dissolved monoclonal antibody recognising another epitope of the IFNα subtype than the carrier-bound monoclonal antibody, and the amount of the IFNα or hybrid IFNα is determined by measuring the radioactivity bound to the carrier. In such a preferred radioimmunoassay either the carrier-bound antibody or the radiolabelled antibody is the monoclonal antibody or a derivative thereof of the present invention as described hereinbefore, the other antibody being a monoclonal antibody to IFNα falling outside the scope of the present invention or a polyclonal antibody, optionally in the form of a radiolabelled derivative.

Particularly preferred is a sandwich radioimmunoassay as described hereinbefore, wherein the monoclonal antibody of the invention is bound to a bead, for example a polystyrene bead, this coated bead is incubated in a test of standard solution containing IFNα or hybrid IFNα and is finally developed with a radiolabelled monoclonal antibody recognizing a different IFNα epitope.

Figure 4:
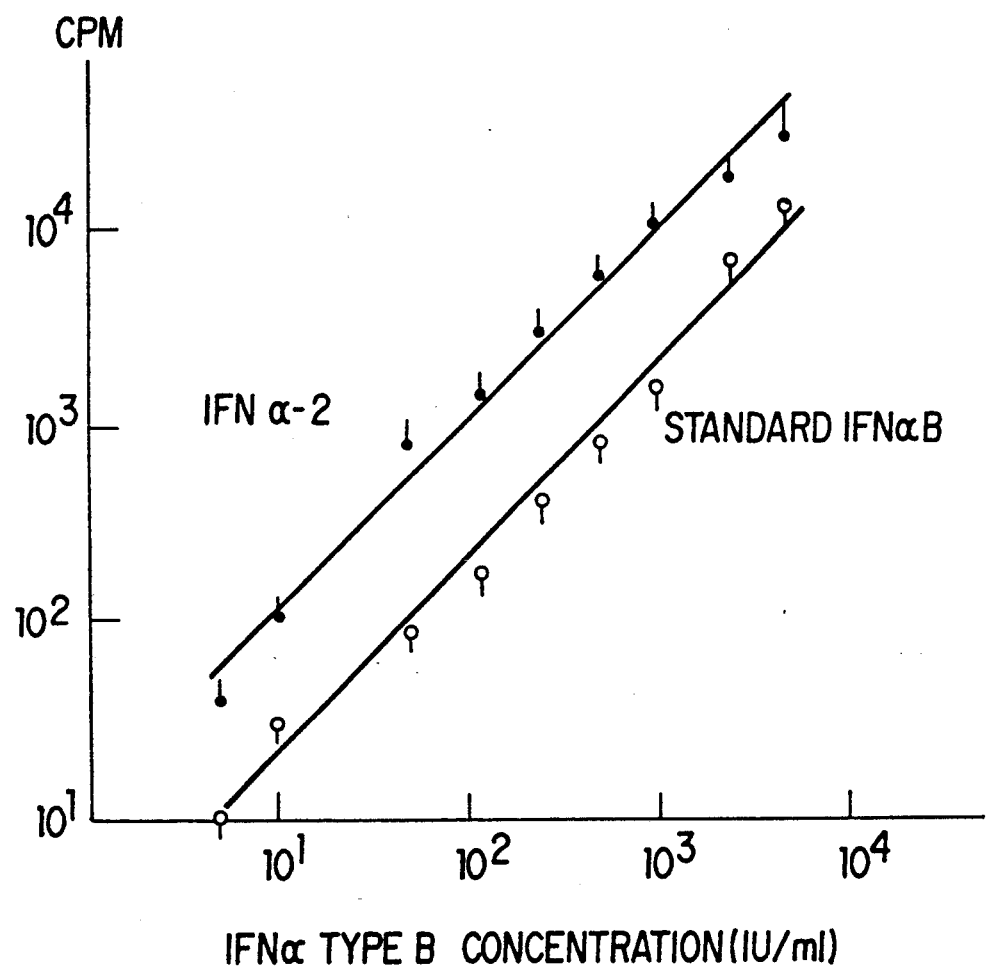
FIG. 4 and FIG. 5 show the radioactivity bound to the carrier bead in function of the quantity of IFN-α-2 in the test solution measured in a sandwich RIA.
Figure 5:
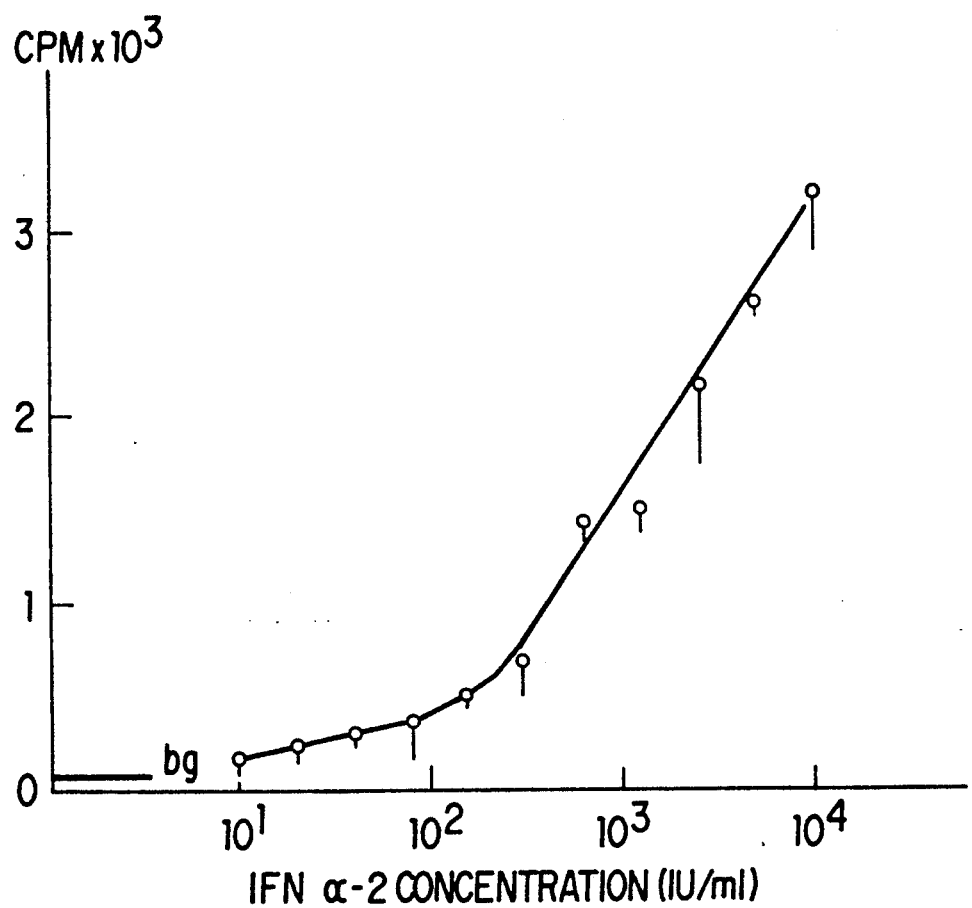

FIGS. 4 and 5 show the radioactivity bound to the carrier bead in function of the quantity of IFN-α-2 polypeptide belonging to the IFNα/B subtype in the test solution as can be measured in a sandwich RIA described in detail in the Experimental Part. The sensitivity of the RIA allows a fast, reliable and quantitative determination of 150 to 5000 IU/ml of IFN-α-2 subtype, or of as little as one IU/ml of IFN-α-2 subtype if a more time-consuming procedure is chosen. Similar results can be obtained in a sandwich RIA for the determination of polypeptides belonging to other IFNα subtypes, e.g. IFNα/D subtype or IFNα/F subtype, and especially of the hybrid interferons according to the invention.

The monoclonal antibody according to the invention can be used as such or in the form of an enzyme-conjugated derivative in an enzyme-immunoassay. Such immunoassays include test procedures in which an enzyme-labelled monoclonal antibody derivative according to the invention, enzyme-labelled antibodies known per se that recognize and bind the epitopes of the anti-IFNα antibody according to the invention or other anti-IFNα antibodies are used.

There is preferred an ELISA (enzyme-linked immunoadsorbent assay) in which a carrier as described above for an RIA is coated with the monoclonal antibody according to the invention, incubated with a test solution containing IFNα and then with a polyclonal serum to IFNα, for example sheep serum, and, finally, the bound antibodies of the polyclonal serum are developed by enzyme-labelled antibodies that recognize and bind to them, and the amount of IFNα bound is determined by an enzyme substrate reaction. Such an enzyme-labelled antibody is, for example, a phosphatase-labelled goat-anti-sheep immunoglobulin.

There is also preferred an ELISA in which a carrier coated with a monoclonal antibody specific for an IFNα subtype is incubated with a test solution containing IFNα and with a solution of a monoclonal antibody that is conjugated with an enzyme, the dissolved monoclonal antibody recognising a different epitope of the IFNα subtype than does the carrier-bound monoclonal antibody. By an enzyme substrate reaction that results, for example, in a colour change and can be observed by eye or with optical measuring devices, the amount of bound enzyme, which is proportional to the amount of IFNα or IFNα hybrid subtype in the test solution, is measured.

Particularly preferred is an enzyme immunoassay called immunodot analysis, in which test or standard solutions containing IFNα or hybrid IFNα are spotted on a microporous carrier with high intrinsic affinity for polypeptides, e.g. on nitrocellulose, the carrier bearing one or several dots of said IFNα containing probes is incubated in a solution of the monoclonal antibody of the invention, then in a solution of an enzyme-labelled second antibody that recognizes and binds the monoclonal antibody of the invention and finally in a solution of an enzyme substrate which leads to a detectable signal, e.g. a coloured substance. Such an enzyme-labelled second antibody is e.g. rabbit anti-mouse immunoglobulin conjugated with horseradish peroxidase which can be developed with suitable enzyme substrates such as 4-chloro-1-naphthol or the like.

The use according to the invention of the monoclonal antibody and derivatives thereof as described hereinbefore for the qualitative and quantitative determination of IFNα subtypes or hybrid IFNα also includes other immunoassays known per se, for example immunofluorescence tests using antibody conjugates or antigen conjugates with fluorescing substances, latex agglutination with antibody-coated or antigen-coated latex particles or haemagglutination with antibody-coated or antigen-coated red blood corpuscles or the like.

The invention relates also to test kits for the qualitative and quantitative determination of IFNα subtypes and hybrid IFNα according to the invention containing the monoclonal antibody 144 BS and/or a derivative thereof and, optionally, other monoclonal or polyclonal antibodies to human IFNα and/or adjuncts.

Test kits according to the invention for a radioimmunoassay contain, for example, a suitable carrier, uncoated or coated with a monoclonal antibody to IFNα, optionally freeze-dried or concentrated solutions of a monoclonal or polyclonal antibody to IFNα and/or a radiolabelled derivative thereof, wherein at least one of the monoclonal antibodies coated on the carrier, in solution or in radiolabelled form is the monoclonal antibody of the invention, standard solutions of human IFNα, buffer solutions and, optionally, polypeptides and detergents for preventing non-specific adsorption and aggregate formation, pipettes, reaction vessels, calibration curves and the like.

Test kits according to the invention for an enzyme immunoassay contain, for example, a suitable carrier, optionally freeze-dried or concentrated solutions of a monoclonal and/or a polyclonal antibody to IFNα and of an enzyme-labelled monoclonal or polyclonal antibody to IFNα or to a first antibody recognising IFNα, wherein at least either the monoclonal antibody to IFNα or the enzyme-labelled antibody derivative to IFNα is the monoclonal antibody or a derivative thereof according to the invention, enzyme substrates in solid or dissolved form, standard solutions of human IFNα, buffer solutions and, optionally, polypeptides and detergents, pipettes, reaction vessels, calibration curves, colour scale tables and the like.

IFNα from natural sources or IFNα subtypes or polypeptides related to IFNα such as the hybrid interferons according to the invention can be purified by immunoaffinity chromatography with the aid of the monoclonal antibody of the invention. The monoclonal antibody or a fragment thereof is bound to a suitable carrier of organic or inorganic origin, such as cross-linked agarose, dextran or polyacrylamide in suitably functionalized form, optionally after activation, applying general methods known in the art. For instance, a carrier bearing activated ester functions is suspended in an aqueous buffer solution, mixed with a solution of the monoclonal antibody or a fragment thereof, filtered, resuspended and washed to remove excess monoclonal antibody, and treated with a solution of irrelevant proteins to block free reactive positions of the carrier. This antibody-coated carrier is used to selectively bind human IFNα subtypes, e.g. IFNα/B, IFNα/D and IFNα/F subtypes and related polypeptides such as the hybrid interferons according to the invention in glycosylated or unglycosylated form. To that end carrier material is suspended in a suitable aqueous solvent, for example a salt solution, such as NaCl solution, or a buffer solution, such as phosphate-buffered NaCl solution, NaHCO$_3$ solution or 3-(N-morpholino)propanesulphonic acid solution, and brought into contact with the solution containing the IFNα, for example is poured into a chromatography column and the solution containing IFNα is introduced and pumped through the carrier material, if desired under pressure. Unbound proteins and other impurities are washed away with aqueous solutions, for example buffer solutions in a pH range of from approximately pH 5 to approximately pH 9 and/or salt solutions, for example NaCl solution. The IFNα bound to the antibody on the carrier material is eluted with suitable aqueous solutions, for example buffer solutions in a pH range of from approximately pH 2 to approximately pH 5, such as glycine buffer or citric acid, or pH gradients of differing composition or salt solutions, for example concentrated NH$_4$SCN solution. The eluate containing IFNα is optionally neutralized, and the purified IFNα is isolated therefrom according to known procedures.

The following Examples serve to illustrate the present invention but should not be construed as a limitation thereof.

EXPERIMENTAL PART

Abbreviations used in the Examples:
DTT: 1,4-dithiothreitol
TNE: solution containing 50 mM Tris.HCl pH 7,5, 100 mM NaCl, 2 mM EDTA
Tris: tris-(hydroxymethyl)-aminomethane
EDTA: ethylenediamine tetraacetic acid
TE: solution containing 10 mM Tris, 50 μM EDTA
N-medium: contains Bacto-Tryptone (10 g, Difco), yeast extract (1 g, Difco), glucose (1 g), NaCl (8 g), CaCl$_2$.2H$_2$O (249 mg) per 1 l solution
TBE: solution containing 89 mM Tris, 89 mM boric acid, 2 mM EDTA
BSA bovine serum albumin
HAT: hypoxanthine/aminopterin/thymidin
Ig: immunoglobulin
IU: international units (of interferon activity)
MAb: monoclonal antibody
PBS: phosphate buffered saline
SDS-PAGE: sodium dodecyl sulfate polyacrylamide gel electrophoresis.

PART I

Construction and cloning of interferon α-2/α-3 hybrids in *Escherichia coli*

All hybrid interferon protein coding sequences described below have been operatively linked to the β-lactamase promoter, cloned into a pBR322 derived expression plasmid and transformed into *E. coil* HB101.

EXAMPLE 1

Construction of PvuII resistant vectors carrying DNA sequences of the lymphoblastoid IFNs α-2 and α-3 pBR322 is cut with PvuII (Biolabs), and the linear DNA is ligated to a [$^{32}$P]-BclI linker [d(ATGTGT-GATCACACAT) synthesized by the solid phase phosphotriester method, cf. H. Rink et al., Nucleic Acids Research 12, 6369 (1984)] as follows:

The restricted plasmid DNA (1 μg, about 0.7 pmole ends) is ligated to $^{32}$P-labelled BclI linker DNA (about 40 pmole ends) in 50 μl reaction volume containing 20 mM Tris-HCl pH 7.8, 10 mM MgCl$_2$, 10 mM DTT, 0.5 mM rATP and 40 U/μl T$_4$ DNA Ligase (Biolabs). After 2-3 h incubation at 15° C., the aqueous phase is extracted with an equal volume of phenol/chloroform, and the DNA is precipitated by the addition of 1/9 volume 10×TNE, 2.5 volumes of ethanol and keeping at −20° C. over night. The DNA pellet is resuspended in 50 μl TE pH 8.0 and centrifuged through a 5-23% sucrose gradient (50 mM Tris-HCl pH 8.0/1 mM EDTA) in a Kontron TST 60 rotor for 4 h at 58,000 rpm and 15° C. The gradient is fractioned from top to bottom, and the radioactivity in each fraction is monitored by Cerenkov counting. Fractions of interest are pooled and the DNA precipitated with TNE and ethanol. The DNA pellet is resuspended in restriction buffer and digested with BClI and again precipitated after extraction of the aqueous phase with phenol/chloroform. This linear DNA is then recirculated at a concentration of 5 μg/ml under conditions identical to those described for the linker ligation.

The ligated DNA is cut with the enzymes HindIII, PvuII (to elimate residual intact pBR322) and PstI, and the HindIII-PstI large fragment (3600 bp+linker) containing the origin of replication and the amp$^R$ gene is isolated by sucrose gradient centrifugation.

Hind III-PstI inserts from CG-pBR(AP)/LyIFN-α-2 (1160 bp) and from CG-pBR(AP)/LyIFN-α-3 (1020 bp) (European Patent Application No. 76,489) obtained by sucrose gradient centrifugation are each ligated into the DNA prepared above, resulting in plasmids pAM4 and pAM2, containing the LyIFN-α-2 and LyIFN-α-3 coding regions, respectively, under the control of the β-lactamase promoter.

Ligated DNA is directly used to transform competent E. coli as follows: The DNA ligation mixture (or fractions of it) is transferred into 150 μl 15 mM Tris-HCl pH 7.5, 10 mM CaCl₂, 10 mM MgCl₂, 10 mM NaCl, 0.5 mM EDTA, and 50 μl of the CaCl₂-treated recipient E. coli HB 101 are added. The mixture is kept at 0° C. for 20 min., then transferred to 42° C. for 2 min., and after cooling to room temperature 1 ml of N-medium is added. The incubation is continued at 37° C. for 1 h (shaker platform, 250 rpm) after which 600 μl are plated on McConkey-Agar (Difco) containing tetracycline (10 μg/ml). The petri dishes are incubated at 37° C. for 16–18 h, when bacterial colonies can be observed.

Plasmid DNA is obtained from the transformants by the following procedure. 10 ml N-medium containing tetracycline (10 μg/ml) is inoculated with one transformant colony each and the cultures are agitated at 37° C. (shaking platform, 150–300 rpm) until they had reached an optical density of 0.9–1.1 (650 nm). The cells are harvested and resuspended in an equal volume of N-medium containing tetracycline (10 μg/ml) and chloramphenicol (80 μg/ml). Incubation is continued at 37° C. for another 18 h to amplify the number of plasmid copies per cell. The bacteria are harvested and the bacterial pellet is resuspended in 50 mM Tris HCl pH 8 (10 ml per gram of wet cell weight) and lysozyme (Sigma) is added to a final concentration of 2 mg/ml. After 10 min at 0° C. the solution is adjusted to 50 mM EDTA, after 10 min at 0° C. Triton×100 is added to a final concentration of 0.8% and the preparation is kept at 0° C. for 1 h followed by centrifugation in a Sorvall SS-34 rotor for 30 min at 18,000 rpm. After extraction of the clear supernatant with phenol followed by two extractions with chloroform RNase A (Sigma) is added to a final concentration of 25 μg/ml and the solution is incubated at 37° C. for 1 h. For removal of RNA, NaCl (1M final concentration) and polyethylene glycol 6000 (7.5% final concentration) are added and the preparation is kept at −10° C. for 2 h, followed by centrifugation for 10 min at 10.000 rpm and 0° C. in a Sorvall SS-34 rotor. The pellets are resuspended in 200 μl TNE and again extracted with phenol/chloroform (1:1) before reprecipitation (by addition of 500 μl ethanol, 5 min at −80° C., 10 min Eppendorf centrifuge). The DNA pellets are resuspended in 20–40 μl of TE. Typical yields resulting from this procedure are about 20 μg of plasmid DNA.

The prepared plasmid DNAs (pAM4 and pAM2) are subjected to restriction enzyme analysis. The structure of pAM4 and pAM2 is confirmed.

EXAMPLE 2

Elimination of the 3' extracistronic PvuII site from pAM 4

Unlike pAM2 (α-3), pAM4 (α-2) still contains two PvuII sites (cf. FIG. 3). In order to facilitate the construction of hybrid IFN genes at the PvuII site within the IFN coding region, the second PvuII site within the extracistronic region is eliminated.

This modification of plasmid pAM4 is essentially a deletion of the 3' extracistronic IFN α-2 cDNA sequence between PstI and the 3' extracistronic PvuII site (see FIG. 3). pAM4 is partially digested with PvuII [5 μg pAM4 in 50 mM NaCl, 6 mM MgCl₂, 6 mM 2-mercaptoethanol, 10 mM Tris.HCl pH 7.5, 1 unit/μg PvuII (Biolabs) added, digest for 5 min. at 37° C., stop by phenol extraction] and is ligated to [$^{32}$P]-PstI linker (Collaborative Research, procedure as described in Example 1). The DNA mixture is transformed into E. coli HB 101 as above and the plasmids of 16 colonies are screened by restriction enzyme analysis using PstI, PvuII and HindIII for the presence of a deletion having the correct size (246 bp). Out of the 16 colonies screened three are unmodified pAM4, one is a multimer, five have a large deletion (620 bp) and seven carries the desired small deletion (246 bp). One clone with a shortened IFN α-2 insert (Hind III-PstI small fragment now 907 bp) is selected and is designated pAM21.

EXAMPLE 3

Construction of Pvu hybrids with crossover sites at amino acid 92

Plasmids pAM2 (α-3) and pAm21 (α-2) are each cut with HindIII and PvuII which results in the excision of DNA fragments (521 bp) containing the β-lactamase promoter sequences and the N-terminal halves of the IFN genes (coding for amino acids 1 to 92). The large and small fragments (about 4 Kb and 521 bp, respectively) are separated by sucrose gradient centrifugation, and the large fragments are dephosphorylated by treatment of 1 μg DNA fragments in 50 μl 50 mM Tris pH 8 with 1 unit of calf intestine alkaline phosphatase per 10 pmole 5' ends for 30 min at 37° C. Hybrid IFN "$B_1B_2D_3D_4$" and "$D_1D_2B_3B_4$" genes are constructed by ligation of the appropriate large and small DNA fragments described above [large HindIII-PvuII fragment (∼4 Kb) from pAM2 ligated to small HindIII-PvuII fragment (521 bp) from pAM21 resulted in type $B_1B_2D_3D_4$ IFN, etc.]. Ligation is carried out in 10 μl volumes containing 20 mM Tris.HCl pH 7.8, 10 mM MgCl₂, 10 mM DTT, 0.5 mM rATP, 40 units/μl T₄DNA ligase (Biolabs) and approximately 500 ng of large DNA fragments, and 20–40 ng of small DNA fragments. After 5 h at 15° C., 5 μl of the ligation mixtures are used to transform E. coli HB101 as above, resulting in about 1000 transformed colonies each. Three colonies are picked each, their plasmid DNA is isolated and is analyzed with the enzymes HindIII, PvuII, EcoR1, TaqI and PstI. Two colonies harbouring plasmid DNAs of the predicted structure [pAM 27 ("$B_1B_2D_3D_4$") and pAM 33 ("$D_1D_2B_3B_4$")] are selected.

EXAMPLE 4

Construction of hybrid IFN genes crossed over at amino acid 150

Plasmids pAM 2 (α-3) and pAM 21 (α-2) are each digested with PvuII and PstI. The DNA fragments are separated by sucrose gradient centrifugation into PvuII-PstI large fragments (about 4 Kb, encoding the N-terminal 92 amino acids of IFNs α-2 and α-3), and PvuII-PstI small fragments (386 and 495 bp in length, respectively, encoding the C-termini of IFNs α-2 and α-3 ). In a second step, the purified PvuII-PstI small fragments from pAM2 and pAM21 are each $^{32}$P-labelled as follows:

The DNA fragments (~1 μg) are each dissolved in 50 μl 50 mM Tris-HCl pH 8.0 and dephosphorylated by treatment with 1 U/10 pmole 5' ends alkaline phosphatase for 30 min. at 37° C. The enzyme is inactivated by incubation for 1 h at 65° C., and the DNA is purified by adsorption and elution from DEAE-Cellulose and precipitated in ethanol. The DNA is phosphorylated in a 20 μl reaction volume containing 50 mM Tris-HCl pH 9.5/10 mM MgCl$_2$/(5 mM DTT, 30–40 μl of lyophilized γ-[$^{32}$P]-ATP (Amersham, 6000 Ci/mmol, 1 mCi/ml) and 0.5 U/μl T$_4$ Kinase (P. L. Biochemicals). After 20 min. at 37° C., the reaction is stopped by adding EDTA to 10 mM. An excess (~4 μg) of corresponding untreated DNA fragment is then added, and the solution is extracted with phenol and chloroform. DNA is separated from residual γ-[$^{32}$P]-ATP by chromatography through Sephadex G-50 in TNE. The excluded peak fractions as monitored by Cerenkov counting are pooled and precipitated with ethanol.

The $^{32}$P labelled PvuII-PstI small fragments are each digested completely with Sau3A, and the restricted DNA is separated by electrophoresis in a 6% polyacrylamide gel using TBE as running buffer. 4 DNA fragments corresponding to PvuII-Sau3A (172 bp each, encoding amino acids 93 to 150 of IFNs α-2 and α-3), and to Sau3A-PstI (214 bp and 323 bp, respectively encoding amino acids 151 to 166 of IFNs α-2 and α-3) are isolated from the gel.

By religation of 3 appropriate fragments (see Table 2), 4 hybrid IFN types crossed over at amino acid 150 are generated. The corresponding plasmids are reconstructed in a series of steps; in a first ligation reaction equimolar amounts of PvuII-Sau3A and Sau3A-PstI DNA fragments are ligated in 10 μl of ligation buffer containing 20 mM Tris.HCl pH 7.8, 10 mM MgCl$_2$, 10 mM DTT, 0.5 mM rATP and 40 units/μl T4 DNA ligase for 3–6 hours at 15° C. (resulting in concatemeric DNA). After digestion with PvuII-PstI and extraction with phenol/chloroform (1:1), an excess of the appropriate PvuII-PstI large fragment [dephosphorylated: typically 1 μg of DNA in 50 μl 50 mM Tris.HCl pH 8 (about 0.6 pmole 5' ends) treated with 0.06 units of calf intestine alkaline phosphatase for 30 min at 37° C] is added and the DNA is ligated again. E. coli HB 101 is transformed and 4 clones carrying DNA of the predicted structure as determined by restriction analysis (PvuII, Sau3A, TaqI and EcoRI) are picked. The clones are designated E. coli HB 101 pJC334, pJC37, pJC342 and pJC344 (cf. Table 2).

TABLE 2

Origin of DNA fragments used for construction of the hybrid IFNs crossed over at amino acid 150. In brackets the IFN type and the section of αIFN encoded on the fragments are indicated.

| resultant hybrid IFN type | clone and plasmid designation | ligated DNA fragments (length) | | |
|---|---|---|---|---|
| | | PvuII-PstI (about 4Kb) | PvuII-Sau3A (170 bp) | Sau3A-PstI (210 bp, α-2) (320 bp, α-3) |
| "D$_1$D$_2$D$_3$B$_4$" | pJC334 | AM2(α-3$_{1-92}$) | Am2(α-3$_{93-150}$) | Am21(α-2$_{151-166}$) |
| "D$_1$D$_2$B$_3$D$_4$" | pJC337 | AM2(α-3$_{1-92}$) | Am21(α-2$_{93-150}$) | Am2(α-3$_{151-166}$) |
| "B$_1$B$_2$D$_3$B$_4$" | pJC342 | AM21(α-2$_{1-92}$) | Am2(α-3$_{93-150}$) | Am2(α-2$_{151-166}$) |
| "B$_1$B$_2$B$_3$D$_4$" | pJC344 | AM21(α2$_{1-92}$) | Am21(α-2$_{93-150}$) | Am2(α-3$_{151-166}$) |

EXAMPLE 5

Construction of hybrid IFN genes crossed over at amino acid 60

The construction of these hybrid IFN genes is accomplished by essentially the same procedure as described in Example 4.

Plasmids pAM2 (α-3) and pAM21 (α-2) are each cut with HindIII and PvuII, and the fragments are separated by sucrose gradient centrifugation. The HindII-PvuII small fragments (521 bp, containing the β-lac promoter region and encoding the N-terminal 92 amino acids of IFNs α-2 and α-3) are $^{32}$P-labelled and partially digested with Sau3A (0.5 units of enzyme per μg of DNA, 5 minutes at 37° C., stop reaction by phenol extraction). The resulting mixture of fragments is resolved by electrophoresis in 6% polyacrylamide gels, and 4 fragments (two 424 bp HindIII-Sau3A fragments and two 97 bp Sau3A-PvuII fragments) are extracted from the gel. Religation of 3 appropriate fragments by the stepwise procedure as described in Example 4 (see Table 3), and transformation into E. coli HB 101 results in transformants of only 2 of the expected 4 constructions: pAM65 ("D$_1$B$_2$D$_3$D$_4$") and pAM90 ("B$_1$D$_3$B$_3$B$_4$").

TABLE 3

Origin of DNA fragments used for the construction of two hybrid IFN genes crossed over at amino acid 61. In brackets the IFN type and the section of αIFN encoded on the fragments are indicated.

| resultant hybrid IFN type | clone and plasmid designation | DNA fragment type (length) | | |
|---|---|---|---|---|
| | | HindIII-Sau3A (424 bp) | Sau3A-PvuII (97 bp) | HindIII-PvuII (about 4Kb) |
| D$_1$B$_2$D$_3$D$_4$ | pAM65 | Am2(α-3$_{1-61}$) | Am21(α-2$_{62-92}$) | AM2(α-3$_{93-166}$) |
| B$_1$D$_2$B$_3$B$_4$ | pAM90 | Am21(α-2$_{1-61}$) | Am2(α-3$_{62-92}$) | AM21(α-2$_{93-166}$) |

For the construction of the other two hybrid IFN genes crossed over at amino acid 61, the plasmids pAM65 and pAM90 are each cut with HindIII and PvuII, and the small HindIII-PvuII DNA fragments (521 bp) are isolated after electrophoresis in agarose gels. Ligation of the HindIII-PvuII small fragment of pAM90 with the HindIII-PvuII large fragment of pAM2 results in pAM94 (B$_1$D$_2$D$_3$D$_4$), and ligation of the small HindIII-PvuII fragment of pAM65 with the HindIII-PvuII large fragment of pAM21 yields plasmid pAM76 (D$_1$B$_2$B$_3$B$_4$). The structure of the 4 above plasmid DNAs is confirmed by restriction enzyme analysis.

The respective clones are referred to as E. coli HB101 pAM65, pAM90, pAM94 and pAM76.

PART II

Construction and clonsing of interferon α-2/α-3 hybrids in Saccharomyces cerevisiae All hybrid interferon protein coding sequences described below have been linked to the PH05 promoter and the PH05 transcription termination signals, cloned into the yeast 2μ vector pJDB207, and transformed into yeast strain S. cerevisiae GRF18.

EXAMPLE 6

Construction of expression plasmid p31RT (Δ72)

Plasmid pJDB207/IF2($5_1$)Δ72 (European Patent Application No. 100,561) is digested with HindIII and EcoRI and a 470 bp fragment comprising the carboxyl-terminal end of interferon α-2 and PH05 transcription termination signals is isolated by agarose gel electrophoresis and electroelution [R. Yang et al. Methods Enzym. 68, 176 (1979)] using Micro-Collodion Bags (Sartorius, Göttingen, FRG). Plasmid p31R (cf. EP 100,561) is digested with HindIII and EcoRI and the 4.1 kb vector part is isolated using the same technique. After ligation of 200 ng of vector and insert DNA using E. coli T4 DNA ligase and transformation of E. coli HB 101 to ampicillin resistance a plasmid called p31RT(Δ72) containing the PH05 promoter, the C-terminal end of interferon α-2 and PH05 transcription termination signals is isolated and its structure is confirmed by restriction analysis.

EXAMPLE 7

Construction of plasmids pJDB207 PH05/IFN AM104, AM114 and AM 119

PH05 expression plasmid p31RT(Δ72) (see example 6) is digested with EcoRI and XhoI and the recessed 3' ends are filled in with dCTP, dGTP, dATP and dTTP using the Klenow fragment of DNA polymerase I of E. coli. The blunt ends are subsequently dephosphorylated with bacterial alkaline phosphatase. Plasmids pJC334, pAM90 and pJC337 (Examples 4 and 5) are digested with TaqI (pJC334 and pAM90), or with TaqI and EcoRI (pJC337), and the 3' recessed ends are filled with the corresponding deoxynucleotides as described above. DNA fragments of approximately 560 base pairs are isolated by agarose gel electrophoresis and electroelution using Micro-Collodion Bags as above. Ligation of 200 ng prepared vector part of plasmid p31RT(Δ72) and 200 ng eluted DNA fragments using T4 DNA ligase and transformation of E. coli HB 101 to ampicillin resistance gives rise to plasmids p31R/IFN AM104, (containing the hybrid interferon "$D_1D_2D_3B_4$" coding sequence), p31R IFN AM119 (containing the hybrid interferon "$B_1D_2B_3B_4$" coding sequence) and p31R IFN AM114 (containing the hybrid interferon "$D_1D_2B_3D_4$" coding sequence), respectively. By cutting these plasmids with BamHI and HindIII a DNA fragment of approximately 1300 bp of the configuration PH05 promoter - IFN protein coding sequence - PH05 transcription termination signal is isolated by agarose gel electrophoresis and electroelution. This fragment is cloned between the HindIII and BamHI sites of plasmid pJDB207. The plasmids are transformed into yeast strain GRF18 to Leu+ (cf. EP 100,561, cf. also Example 14). The resulting clones are referred to as S. cerevisiae GRF 18/pJDB207 PH05/IFN AM104, GRF18/pJDB207 PH05/IFN AM114 and GRF18/pJDB207 PH05/IFN AM119.

EXAMPLE 8

Construction of plasmid pJDB207 PH05/IFN AM129

Plasmid pAM94 (Example 5) is completely cut with TaqI and partially (in the presence of 10 ng/ml ethidium bromide) with EcoRI. A DNA fragment of about 580 bp is isolated by agarose gel electrophoresis and electroelution and ligated to the EcoRI and XhoI cut, gel purified, vector part of plasmid p31RT(Δ72) (cf. Example 6). After transformation of E. coli HB101 to ampicillin resistance the plasmid p31R PH05/IFN AM129 is isolated. This plasmid containing the interferon "$B_1D_2D_3D_4$" coding region is digested with HindIII and BamHI, and the 1300 bp DNA fragment is ligated into pJDB207 as described in Example 7. The plasmid is transformed into yeast strain GRF 18 as above. The resulting clone is designated S. cerevisiae GRF18/pJDB 207 PH05/IFN AM129.

EXAMPLE 9

Construction of plasmids pJDB207 PH05/IFN AM106, AM110 and AM112

Plasmids pJDB207 PH05 IFN/AM 104, AM114 and AM129 (see Examples 7 and 8) are digested with BamHI and PvuII and the 6.8 Kb vector parts containing the respective C-terminal ends of the interferon coding regions are isolated by agarose gel electrophoresis and electroelution. Likewise, plasmid pJDB207R/(α-2)Δ72 (European Patent Application No. 100,561) is digested with BamHI and PvuII and a DNA fragment of 800 bp is isolated. Ligation of the corresponding fragments and transformation of E. coli HB101 gives rise to plasmids pJDB207 PH05/IFN AM106 (containing the hybrid interferon "$B_1B_2B_3D_4$" coding region). AM112 (containing the hybrid interferon "$B_1B_2D_3B_4$" coding region) and AM110 (containing the hybrid interferon "$B_1B_2D_3D_4$" coding region). Yeast strain GRF18 is transformed as usual. The resulting clones are referred to as S. cerevisiae GRF18 pJDB207 PH05/IFN AM106, pJDB207 PH05/IFN AM112 and pJDB207 PH05/IFN AM110.

EXAMPLE 10

Construction of plasmids pJDB207 PH05/IFN DM 1 and DM 2

Plasmid pJDB207 PH05/IFN AM119 (Example 7) is digested with HindIII and BglII and the 7.5 Kb vector part containing the N-terminal end of the interferon coding region is isolated by agarose gel electrophoresis and electroelution. Likewise, plasmids pJDB207 PH05/IFN AM114 and pJDB207 PH05/IFN AM104 (see Example 7) are each digested with the same enzymes and DNA fragments of about 600 bp containing the C-terminal end of the interferon coding region are isolated. The corresponding fragments are ligated with T4 DNA ligase. After transformation of E. coli HB101 plasmids pJDB207 PH05/IFN DM1 containing the hybrid interferon "$B_1D_2B_3D_4$" coding region and pJDB207 PH05/IFN DM2 containing the hybrid interferon "$B_1D_2D_3B_4$" coding region are obtained. Yeast strain GRF 18 is transformed as described above. The resulting clones are referred to as S. cerevisiae GRF18 pJDB207 PH05/IFN DM1 and S. cerevisiae GRF18 pJDB207 PH05/IFN DM2.

EXAMPLE 11

Construction of plasmid pJDB207 PH05/IFN HRi43

Plasmid pJDB207R/IF(α-2)Δ72 (European Patent Application No. 100,561) is digested with BamHI and PvuII and a DNA fragment of 6.8 kb is isolated. Likewise plasmid pJDB207R/IF(α-3) (EP 100,561) is digested with the same enzymes and a DNA fragment of 800 bp is isolated. Ligation of the two DNA fragments and transformation of *E. coli* HB101 to ampicillin resistance gives plasmid pJDB207 PH05/IFN HRi43 containing the hybrid interferon "$D_1D_2B_3B_4$" coding region. Yeast strain GRF18 is transformed as above. The resulting clones are referred to as *S. cerevisiae* GRF18 pJDB207 PH05/IFN HRi43.

EXAMPLE 12

Transformation of Saccharomyces cerevisiae GRF18 and induction of interferon production Plasmid pJDB207 PH05/IFN AM129 ("$B_1D_2D_3D_4$") is introduced into *Saccharomyces cerevisiae* strain GRF18 (α, his 3-11, his 3-15, leu 2-3, leu 2-112, can$^R$) in analogy as described (Hinnen et al., Proc. Natl. Acad. Sci., U.S.A. 75, 1929 (1978)) One μg plasmid DNA is added to 100 μl of a spheroplast suspension and the mixture is treated with polyethylene glycol. The spheroplasts are mixed with 10 ml regeneration agar and plated onto yeast minimal medium plates without leucine. After incubation for 3 days at 30° C., about 1000 transformed cells are obtained.

One single yeast colony from the yeast transformation plates [named *Saccharomyces cerevisiae* GRF 18/pJDB207 PH05/IFN AM129] is picked into 10 ml of yeast minimal medium in a 100 ml Erlenmeyer flask, and grown at 30° C. at 200 rpm for 24 hrs to a density of about $2-3 \times 10^7$ cells/ml. The cells are washed once with 20 ml of low-$P_i$ minimal medium [as "Difco yeast minimal medium without amino acids" supplemented with 20 g/l glucose, but prepared from the components according to the recipe of Difco (Difco Manual, Difco Laboratories, Detroit, U.S.A.) except that 0.03 g/l KH$_2$PO$_4$ plus 1 g/l KCl is used instead of 1 g/l KH$_2$PO$_4$]. Three ml of the resuspended cells are used to inoculate 300 ml low-$P_i$ minimal medium and 300 ml normal minimal medium, respectively, in 1000 ml Erlenmeyer flasks. Incubation is at 30° C. at 160 rpm. Induction of the PH05 promoter is followed by measuring the appearance of acid phosphatase activity in whole cells as described (Toh-e et al., J. Bacteriol. 113, 727 (1973). The cells are grown to about $1-2 \times 10^7$ cells/ml (26–30 hrs of incubation).

EXAMPLE 13

Preparation of yeast cell extracts and determination of the interferon titre Cells from the 300 ml culture medium (see Example 12) at a density of $1-2 \times 10^7$/ml are collected by centrifugation in a Sorvall GSA rotor for 5 min at 8000 rpm at 4° C. The cells are washed once with 100 ml H$_2$O, resuspended in 6 ml ice cold lysis mix [0.1M potassium phosphate buffer pH 7.4, 1% (v/v) Triton X-100,0.0001M PMSF (Merck)] and transferred to a 30 ml corex tube. The suspension is centrifuged again for 5 min in a Sorvall SS-34 rotor at 8000 rpm at 4° C. and resuspended in 3 ml lysis mix at 0° C. Four grams of glass beads (0.4 mm in diameter) are added to the cells and the suspension is shaken on a Vortex Mixer (Scientific Instruments Inc., U.S.A.) at full speed for 30 sec and then cooled for 1 min in an ice bath. This shaking procedure is repeated 5 to 10 times until more than 90% of cells are broken (check under light microscope). Cell debris and glass beads are removed from the solution by centrifugation for 10 min at 8000 rpm at 4° C. in a Sorvall HB-4 rotor. The supernatant is transferred to Eppendorf tubes, frozen in liquid nitrogen and stored at −60° C. Interferon activity is determined according to S. Rubinstein et al. [J. Virol 37, 755 (1981)] to be $7 \cdot 10^9$ units/ml cell extract.

In an analogous manner as described in Examples 12 and 13, *S. cerevisiae* strain GRF18 is transformed with plasmids pJDB207 PH05/IFN AM119 ("$B_1D_2B_3B_4$"), AM106 ("$B_1B_2B_3D_4$"), AM112 ("$B_1B_2D_3B_4$"), DM1 ("$B_1D_2B_3D_4$"), DM2 ("$B_1D_2D_3B_4$"), AM110 ("$B_1B_2D_3D_4$") and HRi43 ("$D_1D_2B_3B_4$"). The resulting strains are cultured. The cells are harvested and the interferon titres are determined as above. The IFN titres are as follows:

*S. cerevisiae* GRF18/pJDB207 PH05/IFN AM119: $5 \cdot 10^9$ units/ml
*S. cerevisiae* GRF18/pJDB207 PH05/IFN AM106: $7 \cdot 10^7$ units/ml
*S. cerevisiae* GRF18/pJDB207 PH05/IFN AM112: $2 \cdot 10^8$ units/ml
*S. cerevisiae* GRF18/pJDB207 PH05/IFN DM1: $3 \cdot 10^9$ units/ml
*S. cerevisiae* GRF18/pJDB207 PH05/IFN DM2: $5 \cdot 10^9$ units/ml
*S. cerevisiae* GRF18/pJDB207 PH05/IFN AM110: $3 \cdot 10^8$ units/ml
*S. cerevisiae* GRF18/pJDB207 PH05/IFN HRi43: $1 \cdot 10^9$ units/ml.

Under the same conditions, *S. cerevisiae* strains GRF18/pJDB207R/IF(α-2) and /IF (α-3) (EP 100,561) give titres of $1 \cdot 10^8$ and $3 \cdot 10^9$ units/ml, respectively.

EXAMPLE 14

Production of hybrid interferon "$B_1D_2D_3D_4$" by transformed yeast cells on a 30 l scale Yeast strain GRF 18 bearing the plasmid pJDB207 PH05/IFN AM129 encoding the gene for hybrid interferon "$B_1D_2D_3D_4$" downstream from the acid phosphatase promoter PH05 is streaked onto the surface of an agar culture of YNB medium. The plate is incubated at 30° C. until confluent growth is observed. A sterile loop is used to transfer a portion of the surface culture to a shake flask containing the pre-culture medium, IFN/21 containing Yeast extract (Difco): 10.0 g
L-asparagine.H$_2$O: 6.6 g
KH$_2$PO$_4$: 1.0 g
MgSO$_4$.7H$_2$O: 1.9 g
L-histidine: 0.02 g
D-glucose (monohydrate): 33.0 g per 1 deionised water.

The 500 ml flask has a single baffle and contains 100 ml of medium. The medium is prepared using deionised water and has a pH value of approximately 6.0. The glucose is sterilised separately. After inoculation the first pre-culture is incubated for 24 h at 30° C. on an orbital shaker with 5 cm throw at a speed of 250 rev/min. The first pre-culture flask provides the inoculum for the second pre-culture flasks. These flasks receive an inoculum of 1% v/v. The medium and incubation conditions are identical with those for the first pre-culture.

Sufficient flasks from the second pre-culture stage are combined to provide 1% v/v inoculum for the 30 l fermenter (3 flasks/fermenter). The production fermenter has an operating volume of 30 l, contains four baffles and a single six-bladed disc turbine agitator with a diameter of 115 mm. The agitation rate is 600 rev/m... air is sparged at 1 vol/vol/min and the overpressure is maintained at 0.3 bar. The fermentation temperature is 30° C. The fermenter is sterilised with medium IFN/23 containing
Yeast extract (Difco): 2.0 g
L-aspargine.H$_2$O: 6.6 g
MgSO$_4$.7H$_2$O: 1.0 g
L-histidine: 0.02 g
D-glucose (monohydrate): 33.0 g per 1 l deionised water.
glucose being sterilised separately and added to give a final volume of 30 l.

After inoculation the fermentation pH value is controlled so that it does not fall below 6.0 by addition of sodium hydroxide. The fermentation has a duration of about 18 h or until the maximum yield of interferon is reached.

The optical density which is a convenient measure of the growth of the yeast reaches a value between 6–7 OD units. The glucose is largely but not completely consumed and there is an induction of acid phosphatase activity concomitant with the production of interferon.

The interferon titre can be measured in crude extracts prepared by mechanical cell discription in the laboratory and is $7 \cdot 10^9$ units/l cell extract. The protein content of the crude extract is approximately 1 mg/ml.

At the end of the fermentation the culture broth may be cooled to 10° C. if necessary prior to harvesting and recovery of the hybrid interferon.

30 l culture broth of pH 6.0 is cooled to 10° C. and the cells are separated with a Sharples ® centrifuge. The clear supernatant contain no IFN activity. The obtained cell mass is adjusted with Buffer X (2 mM Tris pH 8.0, 5 mM EDTA, 0.5M NaCl, 20 μM phenylmethylsulphonylfluoride) to 1400 ml and has a pH value of 8.0. After cooling to 5°–10° C. the suspension is passed through a DYNO ®-Mill (type KDL Pilot, 0.6 l) provided with polyurethane agitator disks and 500 ml glass beads of 0.5–0.75 mm diameter and having an agitation speed of 3,000 rpm and a feed rate of 10 l/h, whereby the cells are disrupted. The suspension has a pH value of 8. The suspension containing the broken cells is clarified by centrifugation. The centrifugation is performed in a Sorvall 6SA rotor at 12,000 rpm at 4° C. for 20 min.

The strain *S. cerevisiae* GRF18 bearing the plasmid pJDP207 PH05/IFN AM119, AM106, AM112, DM1 and DM2, respectively, can be cultured and a clarified solution containing the corresponding hybrid interferon can be produced in an analogous manner.

EXAMPLE 15

Preparation of extracts of *E. coli* strain HB101/pAM94 and determination of IFN activity

*E. coli* strain HB101/pAM94 is grown to an optical density of 8 at 650 nm in 1 liter of M 9 medium containing 0.4% casamino acids and 2% glucose. Cells are sedimented and resuspended in buffer (16 g cells in 160 ml buffer) containing 0.1M Tris-HCl pH 8.0, 0.5M NaCl, 5 mM EDTA and 100 μM PMSF. Lysozyme is added to a final concentration of 1 mg/ml. The solution is then kept on ice for 30 min. The cells in this suspension are opened using a Sorvall Omnimix at a setting of three times for 60 seconds. The suspension containing the broken cells is clarified by centrifugation in a Sorvall 6SA rotor at 12,000 rpm at 4° C. for 20 min. The supernatant is assayed for IFN activity using the method of S. Rubinstein et al. (supra).

An IFN activity of $5 \cdot 10^7$ units/ml cell extract is found.

In an analogous manner, *E. coli* strains HB101/pAM90, pJC344 and pJC342 are cultured and the interferon titres are determined as above to be $5 \cdot 10^8$, $5 \cdot 10^7$ and $5 \cdot 10^6$ units/ml cell extract.

EXAMPLE 16

Preparation of hybridoma cells a) Source of immunogen:
A sample of semi-purified natural human leukocyte IFN (IFNα) obtained from Dr. K. Cantell (Helsinki) with a specific activity of $13 \times 10^6$ IU per mg protein is used for the immunizations.

b) Immunization protocol:
Seven female Balb/c mice (Tierfarm Sisseln, Switzerland) 10–14 weeks old are immunized by injection into the four footpads of $4 \times 10^5$ IU of IFNα (Example 16a) emulsified in complete Freund's adjuvant (Difco). A further injection of $4 \times 10^5$ IU of IFNα in incomplete Freund's adjuvant is given at day 30, and a booster injection (i.p.) of $6 \times 10^5$ IU of IFNα in PBS at day 60. Three days later the spleens are taken for the fusion.

c) Cell fusion:
All fusion experiments are performed according to the procedure of G. Köhler and C. Milstein (Nature 256, 495 (1975)) using the nonsecreting Sp 2/O-Ag14 myeloma line (M. Shulman, C. D. Wilde and G. Köhler, Nature 276, 269 (1978)). $10^8$ spleen cells are mixed with $10^7$ myeloma cells in the presence of 1 ml of 50% polyethylene glycol (PEG 1500, Serva). After washing, the cells are resuspended in 48 ml of standard Dulbecco's minimum essential medium (Gibco No. 0422501). $3 \times 10^6$ normal mouse peritoneal exsudate cells per fusion are added as feeder cells. The cells are distributed into $48 \times 1$ ml costar wells and fed 3 times per week with standard HAT selection medium for 3 to 6 weeks. When the growth of hybridoma cells becomes visible, the supernatants are screened by a combined immuno-precipitation-bioassay (Example 19). Out of a total of 221 hybridomas, 10 hybridomas are found to produce anti-IFNα antibodies. The hybridoma cells are cloned by limiting dilution in microtiter plates at least once. Hybridoma 144 BS is selected for further studies because it is particularly stable and secretes large quantities of immunoglobulin.

EXAMPLE 17

Isolation and purification of monoclonal antibody

Balb/c mice 8–10 weeks of age (Tierfarm Sisseln, Switzerland) are pretreated intraperitoneally with 0.3 ml pristane (Aldrich). 2–3 weeks later, $2–5 \times 10^6$ cloned hybridoma cells and 0.2 ml pristane are inoculated intraperitoneally. After 8–10 days ascites fluid is collected, centrifuged at $800 \times g$ and stored at $-20°$ C.

Defrosted ascites fluid is centrifuged at $50,000 \times g$ for 60 min. A fat layer floating on the surface is carefully removed, and the protein concentration is adjusted to a concentration of 10–12 mg/ml. Crude immunoglobulin is precipitated by dropwise addition of 0.9 volume equivalents of saturated ammonium sulphate at 0° C., then dissolved in 20 mM Tris-HCl/50 mM NaCl (pH 7.9) and dialysed against the same buffer. An immunoglobulin fraction is obtained by DEAE-D52 cellulose (Whatman) chromatography using a buffer gradient system of 20 mM Tris-HCl/25–400 mM NaCl, pH 7.9. The immunoglobulin is again precipitated with ammonium sulphate and dissolved in PBS at a concentration of 10 mg/ml.

Sodium dodecyl sulphate polyacryl amide gel electrophoresis (SDS-PAGE) demonstrates a purity grade of more than 95 percent for the monoclonal antibodies 144 BS.

EXAMPLE 18

Determination of class and subclass of monoclonal antibodies

The class and subclass of monoclonal antibodies produced by cloned hybridoma cells is determined by the known agar-gel immunodiffusion technique of Ouchterlony using class and subclass specific rabbit antibodies (Bionetics). The results are confirmed by an enzyme immunoassay (ELISA) in the following way: Microtiter plates are coated with 1 μg per well of a rabbit immunoglobulin preparation of a class- or subclass-specific serum (Bionetics) in 50 μl of PBS.

Free binding capacity of the plate is saturated with a buffer of 1% bovine serum albumin in PBS containing 0.2% $NaN_3$ (w/v), pH 7.4. 100 μl probes containing monoclonal antibodies are incubated in the wells at 37° C. for 1 h. The plates are washed with PBS, then incubated at 37° C. for 1 h with a phosphatase conjugated rabbit immunoglobulin preparation of the same specificity as used for coating the plates. The fixed enzyme is developed by incubating (37° C., 30 min) with a solution of the enzyme substrate p-nitrophenyl phosphate (1 mg/ml in diethanolamine buffer 10% containing 0.5 mM $MgCl_2$ and 0.02% (w/v) $NaN_3$, pH 9.8) and measuring the optical density at 405 nm. The monoclonal antibodies 144 BS belong to the class $IgG_1K$ (Kappa).

EXAMPLE 19

Combined immunoprecipitation-bioassay

50 μl of crude natural human leukocyte IFN or recombinant IFNα polypeptides (Example 20a) ($10^4$ IU/ml) are mixed with equal amounts of test solution, e.g. the culture supernants of hydribomas or PBS solution of purified monoclonal antibodies, and incubated at 37° C. for 2 hours in microtubes (Eppendorf 3810). Subsequently, 50 μl of previously titrated rabbit anti-mouse Ig antibody (Nordic) is added and the mixture incubated at 37° C. for 1 hour and then at 4° C. for 16 hours whereby free and IFN-bound monoclonal antibodies form immune complexes. The tubes are centrifuged at 12,000 rpm at 4° C. for 5 min. The immune precipitate is washed once with 1 ml cold buffered saline (pH 7.2), then dissolved in 200 μl of buffered saline pH 2.2. The IFN acitivity liberated thereby is determined in a standard bioassay according to J. A. Armstrong, Appl. Microbiol. 21, 723 (1971). Inhibition of cytopathic effect of Mengo virus (400 plaque forming units per well) is assesed by using Hep 2 cells ($3 \times 10^4$ cells per well) in microtiter plates.

EXAMPLE 20

Determination of interferon specificity a) Source of recombinant IFNα polypeptides:
LyIFN-α-1, LyIFN-α-2 and LyIFN-α-3 polypeptides which are related to IFNαF, IFNαB and IFNαD, respectively, are described in European Patent Application No. 76,489. IFNαA and IFNαJ are obtained from Dr. J. Davies (Biogen, Geneva) and Prof. C. Weissmann (University of Zürich, Switzerland), IFNαC from the Weizmann Institute of Science, Department of Virology, Rehovot, Israel.

b) Source of monoclonal antibodies to IFN used for comparison:
Monoclonal antibodies 1K2 and 2K2 are prepared as described in British Patent No. 2,108,510. MAb NK2 and YOK are obtained from Celltech (Berkshire), IY-1 and IY-2 from Inter-Yeda (Israel), S-1, S-2, S-3 and S-4 from Dr. C. Favre, UNICET, Dardilly (France), and MAb I/24 from M. Aguet, University of Zürich (Switzerland).

c) Determination of reactivity of the various monoclonal antibodies to the IFNα subtypes is performed by the combined immunoprecipitation bioassay of Example 19 and the tandem radioimmunoassay described by D. S. Secher, Nature 290, 501 (1981). The results are collected in Table 4.

The monoclonal antibodies 144 BS, 1K2 and 2K2 do not react with human IFNβ (Rentschler, Laupheim, West Germany) or human IFNγ (Bio Science, Emmenbrücke, Switzerland).

TABLE 4

| Monoclonal antibodies | Immunoprecipitation by MAb's of recombinant IFNα subtypes | | | | | |
|---|---|---|---|---|---|---|
| | IFNα subtypes | | | | | |
| | A | α-2 | C | α-3 | α-1 | J |
| 144 BS | + | ++++ | +++ | ++++ | +++ | ++ |
| 1K2 | +++ | − | | +++ | + | +++ |
| 2K2 | ++++ | − | +++ | ++++ | ++ | +++ |
| NK2 | ++++ | ++++ | | − | ++ | ++++ |
| YOK | + | − | | ++++ | − | +++ |
| S-1 | +++ | + | | ++++ | ++ | + |
| S-2 | +++ | − | | − | − | ∓ |
| S-3 | +++ | ++++ | | − | ++ | ++++ |
| S-4 | ++++ | − | | − | + | ++++ |
| IY-1 | ++ | +++ | | − | | ++ |
| IY-2 | ++++ | − | | − | + | +++ |

TABLE 4-continued

| Monoclonal antibodies | Immunoprecipitation by MAb's of recombinant IFNα subtypes |  |  |  |  |  |
|---|---|---|---|---|---|---|
|  | IFNα subtypes |  |  |  |  |  |
|  | A | α-2 | C | α-3 | α-1 | J |
| I/24 | ++++ | ++++ | − | | ++ | ++++ | legend:
++++ 100% binding
++ 50% binding
∓ 10% binding
+++ 75% binding
+ 25% binding
− 0% binding
blank binding not determined
(approximate values)

The results of Table 4 demonstrate that monoclonal antibody 144 BS displays a unique binding pattern. Notable are above all the low binding to IFNαA and the efficient binding to IFN-α-2, IFN-α-3 and IFN-α-1 polypeptides.

Furthermore the results of Table 4 allow the epitope analysis schematically depicted in Table 5.

TABLE 5

| Epitope analysis of recombinant IFNα subtypes |  |  |  |  |  |  |
|---|---|---|---|---|---|---|
| recombinant IFNα subtype | Epitope recognized by monoclonal antibody |  |  |  |  |  |
|  | 144 BS | 1K2 2K2 | NK2, S-3 IY-1, I/24 | YOK | S-1 | S-2 | S-4, IY-2 |
| A | x — XX | — XX | | x — X | | X — XX |
| α-2 | XX | — XX | | | x | — |
| α-3 | XX — XX | | | XX — XX | | |
| α-1 | X — x | X | | X | | x |
| J | X — X | XX | XX — x | | x | — XX |

From the analysis of Table 5 the fact emerges that the epitope combination of each IFNα subtype is unique. Further, the analysis allows the prediction of suitable pairs of monoclonal antibodies for the determination of specific subtypes of IFNα with the exclusion of other subtypes in a tandem immunoassay. For example the combination of monoclonal antibody 144 BS with any of the MAb's NK2, S-3, IY-1, or I/24 will be useful for the detection of IFNαB without interference by IF-NαD, and the combination of the MAb 144 BS with MAb YOK for the detection of IFNαD in presence of IFNαB.

EXAMPLE 21

Preparation of an immunoadsorbent column

One ml of settled Affi-Gel ® 10 (Bio-Rad) is coupled to 17 mg of monoclonal antibody 144 BS according to the manufacturer's instruction: Affi-Gel ® 10 is washed on a sintered glass filter first with cold distilled water and then with a 0.1M NaHCO₃ solution pH 8.0 (coupling buffer). A suspension of 50% gel in coupling buffer is transferred into a plastic tube, mixed with an equal volume of purified monoclonal antibody solution and rotated for 4 hours at room temperature. After coupling the gel is washed with coupling buffer and, in order to block unreacted sites, is treated with 0.1 ml of 1M ethanolamine-HCl (pH 8.0) for 1 to 2 hours at room temperature. The gel is washed with PBS in the presence of 10 mM NaN₃ and kept therein at 4° C.

EXAMPLE 22

Purification of recombinant IFNα by immunoaffinity chromatography

A suspension of broken E. coli cell producing recombinant IFNα, e.g. E. coli HB 101/pAM94 (cf. Example 15) is clarified by centrifugation in a Sorvall 6SA rotor at 12,000 rpm at 4° C. for 20 min. Polyethyleneimine (Polyimin P ®, Fluka, pH 8.0) is added to the supernatant to a final concentration of 0.25% (w/v). The solution is stirred for 1 hour and subsequently centrifuged. The pellet is discarded and the supernatant brought to 65% saturation with solid ammonium sulfate. This mixture is stirred for 1 hour and then centrifuged. The supernatant is discarded and the pellet suspended in one tenth volume (15-20 ml) of PBS (pH 7.2). The solution is dialysed overnight against PBS containing 0.02% NaN₃.

The dialysed solution is mixed with 1 ml of the immunoaffinity gel of Example 21. This mixture is gently agitated for 1 hour, then packed into a column and washed successively with 5 column volumes of PBS, 5 column volumes of PBS containing 0.5M NaCl and 0.2% Triton X-100 ®, and 5 column volumes of PBS. Alternatively, the immunoaffinity gel is packed first into the column and the dialysed solution added on top, then washed as described. The recombinant hydrid IFNα ("B₁D₂D₃D₄") is eluted with an acid buffer pH 2.5 containing 0.1M citric acid and 0.3M NaCl. The active IFN fractions are neutralized with 1M Tris, dialysed against PBS and concentrated to about 0.1 mg/ml protein using ultrafiltration flat bed membranes XM10 (Amicon Corp.).

The maximum capacity of the immunoadsorbent column of Example 21 containing 17 mg of monoclonal antibody 144 BS is about 1.2 mg of each of IFN-α-2 and IFN-α-3 polypeptides, at least 0.8 mg of IFN-α-1 type polypeptide, 1.15 mg hybrid interferon "B₁B₂D₃B₄", 1.25 mg hybrid interferon "B₁D₂B₃B₄", 1.25 mg hybrid interferon "B₁D₂D₃D₄", 0.44 mg hybrid interferon "B₁B₂B₃D₄", 1.6 mg hybrid interferon "B₁D₂B₃D₄", 1.6 mg hybrid interferon "B₁D₂B₃B₄", 1.15 mg hybrid interferon "B₁B₂D₃B₄" and 1.25 mg hybrid interferon "D₁D₂B₃B₄". The immunoadsorbent gel may be used for up to 50 separations without substantial loss of capacity. Recombinant IFN-α-2, IFN-α-3, IFN-α-1 type polypeptides and hybrid interferons purified by this method are homogenous on SDS-PAGE.

EXAMPLE 23

Immunodot analysis

Immunodot analysis is performed according to R. Hawkes et al., Anal. Biochem 119, 142 (1982). Probes containing natural or recombinant interferons are spotted on nitrocellulose sheets at different concentrations. The dots are air dried and the remaining binding capacity of the nitrocellulose blocked by incubation in a Tris buffer (0.15M NaCl, 0.01M Tris-HCl, pH 7.6) containing 10% horse serum. The nitrocellulose strips are then incubated with a solution of monoclonal antibody 144 BS (23 μg/ml), and similarly prepared strips with either a solution of monoclonal antibody 2K2 (30 μg/ml) for comparison, a solution of a normal mouse immunoglobulin (1:100 dilution) as a negative control, or a solution of a polyclonal anti-human interferon α mouse serum (Enzo, 1:1000 dilution) as a positive control. After washing, all strips are treated with rabbit anti-mouse immunoglobulin labelled with peroxidase (Nordic, 1:400 dilution), and the bound second antibody developed with a peroxidase substrate, 4-chloro-1-naphthol.

The monoclonal antibody stains IFNαD type polypeptides (such as IFN-α-3) in concentrations down to 0.4 ng per dot and IFNαB type polypeptides (such as IFN-α-2) at 10 ng per dot, whereas MAb 2K2 recognizes only IFNαD type polypeptides (4 ng per dot).

EXAMPLE 24

Bead-radio-immuno-tandem-assay a) Radiolabelling of monoclonal antibody 144 BS with $^{125}$I:

0.1 mg monoclonal antibody 144 BS are iodinated with $^{125}$I sodium iodide (1 mC) and chloramine T according to a standard method of F. C. Greenwood et al., Biochem. J. 89, 114 (1963). The reaction product is purified with a ion exchange column Bio-Rad ® AG 1×8 and the activity standardized to $4 \times 10^5$ cpm/ml by dilution with PBS.

The iodination of monoclonal antibody 2K2 is performed likewise. Monoclonal antibodies YOK and NK2 are commercially available in radiolabelled form from Celltech.

b) Coupling of monoclonal antibody 144 BS to macro beads:

Polystyrene beads (diameter 6.3 mm, Spherotech AG, Zürich) are incubated at 4° C. for 16 hours by gentle rocking in a solution of 1 mg/ml MAb 144 BS in a coupling buffer of PBS containing 5 mM EDTA and 0.1% NaN$_3$ (pH 8) in a ratio of 20 beads per 10 ml solution. The coated beads are then transferred into a blocking buffer of PBS containing 10% horse serum and 0.1% NaN$_3$ and kept therein at 4° C. until use, at least for 24 hours.

The coupling of other MAb's is performed likewise.

c) Assay procedure:

Plastic tubes (Falcon, 5 ml) are coated with 0.5 ml blocking buffer of PBS containing 10% horse serum and 0.1% NaN$_3$ overnight. The buffer is removed by aspiration, and 0.2 ml of an IFN-containing test or standard solution in blocking buffer added directly to the bottom of the tube. A MAb-coupled and blocked bead of Example 24b) is shortly dried on a clean tissue and carefully transferred without causing foam into the tube containing the IFN solution. The bead is incubated for 4 to 6 hours at room temperature with gentle rocking. The IFN solution is removed by aspiration and each bead washed three times with 2 ml of blocking buffer. The bead is then incubated in 0.2 ml of an $^{125}$I-labelled second antibody (Example 24a) corresponding to $80 \times 10^3$ cpm for 16 hours at 4° C., washed three times with PBS, and transferred into a new tube for counting.

Table 6 presents the results for standard solutions of IFN-α-3 and IFN-α-2 polypeptides obtained with different combinations of solid phase (bead-coupled) first antibody and $^{125}$I-labelled second antibody.

TABLE 6

Selection of suitable monoclonal antibody combination for IFN-α-2 and IFN-α-3 polypeptide assay

| Solid phase antibody | radiolabelled second antibody | cpm per $10^3$ IU/ml found | |
|---|---|---|---|
| | | IFN-α-3 | IFN-α-2 |
| 144 BS | 2K2 | 113 | 105 |
| 144 BS | 144 BS | 103 | 58 |
| 144 BS | YOK | 16,793 | 313 |
| 144 BS | NK2 | 78 | 3,733 |
| 2K2 | 144 BS | 52 | 2 |
| polyclonal | 144 BS | 1,572 | 546 | polyclonal: Bead-coupled, polyclonal sheep anti-IFNα antibody obtained from Celltech.

Best results are obtained with the combination of MAb 144 BS with MAb YOK for the detection of IFN-α-3 and with the combination of MAb 144 BS with MAb NK2 for the detection of IFN-α-2.

FIG. 4 shows the result of quantitative titration experiments with the combination of MAb 144 BS coupled to the solid phase and MAb NK2 in radiolabelled form. The assay gives linear results from 1 to 5000 IU/ml (2 pg/ml to 10 ng/ml) of IFNαB type polypeptides. Differences in the titration curves of IFN-α-2 and "Standard αB" type polypeptide (from Celltech) are due to variations in bioassay measurements of the two IFN preparations.

Similar results are obtained in quantitative experiments for the measurement of IFNαD type polypeptides with the combination of MAb 144 BS coupled to the solid phase and MAb YOK in radiolabelled form. The assay detects reliably down to 1 IU/ml (2 pg/ml) of IFNαD type polypeptides. The combination of MAb 144 BS coupled to the solid phase and MAb NK2 can also be used for the determination of IFNαF type polypeptides.

d) Shortened assay procedure (simultaneous assay):

Using the general procedure described in Example 24c), the MAb-coupled bead is incubated for 3 hours at room temperature with the test solution (0.1 ml) and the radiolabelled second antibody (0.1 ml) together, omitting the washings in between.

FIG. 5 shows that the shortened simultaneous assay can be used reliably for the rapid screening of IFNαB type polypeptide (such as IFN-α-2) samples containing 150 IU/ml or more, but is considerably less sensitive than the assay of Example 24c). bg=background e) Test kit for bead-radio-immuno-tandem assay:

A test kit for the assay described in Example 24c) contains:

100 plastic tubes Falcon 5 ml 100 polystyrene beads 6.3 mm coated with monoclonal antibody 144 BS in PBS containing 10% horse serum and 0.1% NaN$_3$ 20 ml of $^{125}$I labelled monoclonal antibody YOK of a specific activity $4 \times 10^5$ cpm/ml 20 ml of $^{125}$I labelled monoclonal antibody NK2 of a specific activity $4 \times 10^5$ cpm/ml 2 ml standard solution IFN-α-1 containing $10^4$ IU/ml 2 ml standard solution IFN-α-2 containing $10^4$ IU/ml 2 ml standard solution IFN-α-3 containing $10^4$ IU/ml 1000 ml PBS containing 10% horse serum and 0.1% NaN$_3$ calibration curve.

EXAMPLE 25

Enzyme-immunoassay (ELISA)

a) Labelling of monoclonal antibody 144 BS with alkaline phosphatase:

1.4 mg of MAb 144 BS in 1.4 ml of PBS are coupled for 2 hours with a solution containing 5 mg of alkaline phosphatase (SIGMA P6774, type VII-T) according to the standard method of Voller et al., Bull. World Health Organ. 53, 55 (1976), using glutaraldehyde (0.2% v/v). The conjugate is transferred into 5 ml of Tris buffer 0.05M, pH 8.0, containing 1 mmol of $MgCl_2$, 1% BSA and 0.02% $NaN_3$. The solution is kept in the dark at 4° C.

b) Assay procedure:

Polypropylene microtitre plates (Dynatech Labs. Inc.) are coated over a period of 2 hours at 37° C. and overnight at 4° C. with 150 µl of a solution of the monoclonal antibody NK2 (Celltech, 10 µg/ml) in a buffer pH 8.6 (carbonate-buffered 0.9% saline solution containing 0.02% sodium azide). The plates are washed five times with PBS, and protein-reactive sites that are still present are saturated by incubation for 1 hour at 37° C. with 250 µl of a buffer pH 7.4 (0.2% gelatine and 0.2% $NaN_3$ in PBS). Plates coated in this manner can be kept at 4° C. in this buffer for a few days.

50 µl of a dilution series of a test solution or a standard solution containing IFNα subtypes, 50 µl of buffer pH 7.4 and 50 µl of a solution of the phosphatase-labelled antibody 144 BS (Example 25a) that has been diluted 1:100 with buffer pH 7.4 are mixed and incubated in the wells of the microtitre plates for 2 hours at 37° C. and for 30 minutes at 4° C. The plates are washed five times with PBS, then incubated for 30 minutes at 37° C. with 150 µl of a solution of p-nitrophenyl phosphate (1 mg/ml in 10% diethanolamine buffer, 0.5 mM $MgCl_2$, pH 9.8). By measuring the optical density at 405 nm, the amount of released p-nitrophenol is determined, which is proportional to the amount of the bound enzyme phosphatase and hence proportional to the amount of the IFNα subtype in the test solution.

This assay can be used to determine the amount of IFNαB type (such as IFN-α-2) or IFNαF type polypeptides. For the determination of IFNαD type (such as IFN-α-3) polypeptides, the microtitre plate is coated with the monoclonal antibody YOK (Celltech) in place of NK2.

Similar results are obtained, when the microtiter plates are coated with MAb 144 BS, and phosphatase-coupled MAbs NK2 and YOK, respectively, are used as second antibodies.

c) Test kit for ELISA:

A test kit for the assay described in Example 25b contains:
polypropylene microtiter plates,
20 ml of monoclonal antibody NK2 (10 µg/ml) in carbonate-buffered saline (0.9% NaCl, 0.42% $NaHCO_3$, 0.0072% $Na_2CO_3$, 0.02% $NaN_3$)
1 ml of alkaline phosphatase-coupled MAb 144 BS (Example 10.1, 0.3 mg antibody per ml) in Tris buffer (0.05M, 1 mM $MgCl_2$, 1% BSA, 0.02% $NaN_3$, pH 8.0)
2 ml standard solution IFN-α1 containing $10^4$ IU/ml
2 ml standard solution IFN-α-2 containing $10^4$ IU/ml
2 ml standard solution IFN-α-3 containing $10^4$ IU/ml
300 ml PBS
300 ml buffer pH 7.4 (0.2% gelatine and 0.2% $NaN_3$ in PBS)
50 ml of p-nitrophenyl phosphate (1 mg/ml) in diethanolamine buffer (10%, 0.5 mM $MgCl_2$, 0.02% $NaN_3$, adjusted to pH 8.9 with HCl)
calibration curve
colour intensity scale.

EXAMPLE 26

Purification of hybrid interferons using precipitation and chromatographic methods 1 l of interferon "$B_1D_2D_3D_4$" containing solution clarified by centrifugation (cf. Examples 13–15) is acidified using 2M HCl until the solution reaches pH 2.2. The solution is stirred for 1 h at 4° C. and the precipitated protein is separated via centrifugation (GSA rotor Sorvall at 12,000 rpm at 4° C. for 20 min). The pellet is discarded and the supernatant is brought to 30% saturation with solid ammonium sulfate. This solution is stirred for 1 h at 4° C. and then centrifuged. The supernatant containing the interferon is then dialysed against 0.1M $NH_4HCO_3$ at pH 8.2. An interferon activity of about $10^8$ IU/ml is found.

A column containing 50 ml chelating Sepharose 6B (Pharmacia) loaded with $Cu^{2+}$ ions according to the manufacturer's instructions is equilibrated using 250 ml 0.05M sodium acetate pH 7.0 and 0.5M NaCl. 200 ml of dialysed solution (see above) is applied at 4° C. to the column. The column is washed with 150 ml equilibrating buffer. Elution of bound interferon is performed using a linear gradient of 250 ml 0.05M sodium acetate pH 7.0 and 0.5M NaCl 250 ml 0.05M sodium acetate pH 2.8 and 0.5M NaCl and followed by a wash of 150 ml of 0.05M sodium acetate pH 2.8 and 0.5M NaCl.

The active interferon fractions are pooled and dialysed against 0.05M Tris.HCl buffer pH 8.0. Interferon activity in the dialysed solution is approximately $10^8$ IU/ml. The maximum capacity of the column is about 75 mg of interferon "$B_1D_2D_3D_4$".

A column containing 50 ml Q-Sepharose anion exchanger (Pharmacia) is equilibrated using 250 ml 0.05M Tris.HCl buffer pH 8.0. 100 ml of the above dialysed interferon containing solution is applied to the column at room temperature. The column is subsequently washed with 50 ml equilibrating buffer. Bound interferon is eluted using a linear gradient of 0 to 0.7M NaCl in 200 ml 0.05 Tris.HCl pH 8.0.

The pure interferon elutes at about 0.3M NaCl. The active fractions show a single band with an apparent molecular weight of 19,000 when analysed on SDS polyacrylamide gels. The maximum capacity of the anion exchange column is about 50 mg of hybrid interferon "$B_1D_2D_3D_4$".

In an analogous manner, hybrid interferons "$B_1D_2B_3B_4$", "$B_1D_2B_3D_4$", "$B_1D_2D_3B_4$", "$B_1B_2B_3D_4$" and "$B_1B_2D_3B_4$" can be purified.

EXAMPLE 27

Lyophilisation of hybrid interferon "$B_1D_2D_3D_4$"

Interferon "$B_1D_2D_3D_4$" purified either via immunoaffinity chromatography using monoclonal antibody 144 BS or via conventional chromatographic techniques (cf. Example 26) is dialysed against 0.5M $NH_4HCO_3$ and subsequently lyophilised. Small volumes of water are added twice to the lyophilised sample in order to remove $NH_4HCO_3$ completely. The solution is then relyophilised.

Reconstitution of interferon "B₁D₂D₃D₄" solution is performed as follows: 0.5M NH₄HCO₃ pH 8.2 is added to the lyophilised sample to obtain an interferon concentration of about 0.1 mg/ml. The redissolved interferon has a specific antiviral activity of $2 \cdot 10^8$ IU/mg which activity is identical to the corresponding value before lyophilisation.

EXAMPLE 28

Physicochemical characterisation of hybrid interferons

The hybrid interferons according to the invention and the parental interferons are subjected to polyacrylamide SDS gel electrophoresis according to the method described by Laemmli [Nature 227, 680 (1970)]. The apparent molecular weights of the hybrid interferons given in Kilo-Daltons (kD) are summarized in Table 7. Table 7 contains also the isoelectric points (pI) of the hybrid interferons as determined using LKB polyacrylamide gels containing Ampholine ®.

TABLE 7

| Apparent molecular weights and isoelectric points of hybrid interferons. | | |
|---|---|---|
| IFN | app. molecular weight | pI |
| α-2 | 27,000 | 5.2 |
| α-3 | 20,000 | 5.2 |
| B₁B₂D₃D₄ | 27,000 | 5-6 (diffuse) |
| D₁D₂B₃B₄ | 20,000 | 5.0 |
| B₁B₂B₃D₄ | 27,000 | 5.2 |
| B₁B₂D₃B₄ | 26,000 | 5-6 (diffuse) |
| B₁D₂D₃D₄ | 19,000 | 5.4 |
| B₁D₂B₃D₄ | 20,000 | 5.6 |
| B₁D₂D₃B₄ | 20,000 | 5.5 |
| B₁D₂B₃B₄ | 20,000 | 5.4 |

The amino acid sequence of the hybrid interferons according to the invention is determined using a 470 A protein sequencer from Applied Biosystems or using a 890 C Beckman sequencer. In both cases automated Edman degradation is performed. The structure found is in full accordance with the expected one. The N-terminal amino acid is cysteine.

EXAMPLE 29

Effect of hybrid interferons on the level of (2′-5′) oligoisoadenylate synthetase activity in Daudi cells Daudi cells are seeded at $2 \times 10^5$ cells/ml in RPMI 1640 medium with 10% foetal calf serum containing the concentration indicated (cf. Table 8) of hybrid interferons "B₁B₂B₃D₄", "B₁D₂B₃B₄", "B₁D₂D₃D₄" and "B₁B₂D₃B₄". After 24 hours treatment, $5 \times 10^6$ cells per sample are centrifuged (9000 rev/min) and resuspended in 500 μl of cold lysis buffer (20 mM 4-(2-hydroxyethyl)-1-piperazineethanesulfonic acid buffer pH 7.5, 5 mM MgCl₂, 120 mM KCl, 7 mM dithiothreitol, 10% glycerol, 0.5% Nonidet P 40) and incubated for 2 min on ice. The samples are then centrifuged (9000 rev/min, 8 min., 4° C.) and the supernatant is recovered and assayed for (2′-5′)-oligoisoadenylate synthetase activity as follows:

The supernatant is mixed with 50 μl of poly(rI)·(rC) agarose (P-L Biochemicals) for 15 min at 30° C. and the non-adsorbed material is removed by centrifugation. The poly(rI)·(rC)-adsorbed material is incubated with 2.5 mM (α³²P) ATP, 400 Ci/mmol (Amersham International) for 20 h at 30° C., treated with bacterial alkaline phosphatase (Sigma) and then eluted from a column of acid alumina (Sigma) (300 μl) with 3.0 ml of 1M glycine-HCl buffer pH 2.0 as described (Merlin et al. Analyt. Biochem. 110, 190 (1981)). Results in Table 8 are expressed as the fold increase in (2′-5′)-oligoisoadenylate synthetase activity in interferon treated cells relative to the level of enzyme activity in untreated control cells (mean activity $51.6 \pm 8.7$ pmole/hr/$10^5$ cells).

TABLE 8

| IFN concentration [units/ml] | Fold increase in (2′-5′) (A) synthetase activity [pmole ATP incorporated/hr/$10^5$ cells] | | | |
|---|---|---|---|---|
| | 1 | 10 | 100 | 1000 |
| IFN α-2 ("B") | 3.6 | 4.0 | 5.7 | 5.6 |
| α-3 ("D") | 2.2 | 3.2 | 3.2 | 3.9 |
| "B₁B₂D₃D₄" | 3.4 | 3.2 | 4.6 | 4.0 |
| "D₁D₂B₃B₄" | 2.6 | 2.1 | 4.8 | 4.3 |
| "B₁B₂B₃D₄" | 9.4 | 8.4 | 10.0 | 8.5 |
| "B₁D₂B₃B₄" | 5.6 | 5.7 | 7.8 | 11.4 |
| "B₁D₂D₃D₄" | 5.8 | 8.9 | 12.1 | 17.5 |
| "B₁B₂D₃B₄" | 5.6 | 7.0 | 9.1 | 9.6 |

EXAMPLE 30

Pharmaceutical preparation (parenteral administration)

2 mg of hybrid interferon "B₁D₂D₃D₄" having a specific activity of $1.3 \cdot 10^8$ units/mg on human WISH cells, are dissolved in 30 ml of 5N human serum albumin. The resulting solution is passed through a bacteriological filter and the filtered solution is subdivided under aseptic conditions into 100 vials each containing $2.6 \cdot 10^6$ units of pure hybrid interferon. The vials which are suitable for parenteral administration are preferably stored in the cold, for example at −20° C.

In the same manner, vials containing $5.2 \cdot 10^6$ or $1.04 \cdot 10^7$ units may be prepared by using 4 or 8 mg, respectively, of the hybrid interferon.

In an analogous manner, vials containing hybrid interferon "B₁D₂B₃B₄", "B₁B₂D₃B₄", "B₁D₂B₃D₄", "B₁D₂D₃B₄" or "B₁B₂D₃D₄" (specific activities $1.28 \cdot 10^8$, $2 \cdot 10^8$, $7.7 \cdot 10^7$, $3.8 \cdot 10^7$ and $8 \cdot 10^7$, respectively) can be prepared.

We claim:

1. A hybrid vector comprising a DNA sequence coding for a hybrid interferon polypeptide having an amino acid sequence composed of two to four sub-sequences corresponding in amino acid identity and number to sub-sequences of human lymphoblastoid interferons LyIFN-α-2 and LyIFN-α-3, said hybrid interferon polypeptide being selected from the group consisting of a polypeptide having an amino acid sequence consisting of amino acids 1 to 150 of LyIFN-α-2 and amino acids 151 to 166 of LyIFN-α-3, a polypeptide having an amino acid sequence consisting of amino acids 1 to 92 of LyIFN-α-2, amino acids 93 to 150 of LyIFN-α-3 and amino acids 151 to 166 of LyIFN-α-2, and a polypeptide having an amino acid sequence consisting of amino acids 1 to 60 of LyIFN-α-2, amino acids 61 to 92 of LyIFN-α-3, amino acids 93 to 150 of LyIFN-α-2 or of LyIFN-α-3 and amino acids 151 to 166 of LyIFN-α-2 or of LyIFN-α-3.

2. A hybrid vector according to claim 1, wherein the DNA sequence codes for the hybrid interferon polypeptide "B₁B₂B₃D₄" having the formula CYS ASP LEU PRO GLN THR HIS SER LEU GLY ASN ARG ARG ALA LEU ILE LEU
LEU ALA GLN MET ARG ARG ILE SER PRO PHE SER CYS LEU LYS ASP ARG HIS -continued
ASP PHE GLU PHE PRO GLN GLU GLU PHE ASP ASP LYS GLN PHE GLN LYS ALA
GLN ALA ILE SER VAL LEU HIS GLU MET ILE GLN GLN THR PHE ASN LEU PHE
SER THR LYS ASP SER SER ALA ALA LEU ASP GLU THR LEU LEU ASP GLU PHE
TYR ILE GLU LEU ASP GLN GLN LEU ASN ASP LEU GLU SER CYS VAL MET GLN
GLU VAL GLY VAL ILE GLU SER PRO LEU MET TYR GLU ASP SER ILE LEU ALA
VAL ARG LYS TYR PHE GLN ARG ILE THR LEU TYR LEU THR GLU LYS LYS TYR
SER SER CYS ALA TRP GLU VAL VAL ARG ALA GLU ILE MET ARG SER LEU SER
LEU SER THR ASN LEU GLN GLU ARG LEU ARG ARG LYS GLU.

3. A hybrid vector according to claim 1, wherein the DNA sequence codes for the hybrid interferon polypeptide "B₁B₂D₃B₄" having the formula CYS ASP LEU PRO GLN THR HIS SER LEU GLY ASN ARG ARG ALA LEU ILE LEU
LEU ALA GLN MET ARG ARG ILE SER PRO PHE SER CYS LEU LYS ASP ARG HIS
ASP PHE GLU PHE PRO GLN GLU GLU PHE ASP ASP LYS GLN PHE GLN LYS ALA
GLN ALA ILE SER VAL LEU HIS GLU MET ILE GLN GLN THR PHE ASN LEU PHE
SER THR LYS ASP SER SER ALA ALA LEU ASP GLU THR LEU LEU ASP GLU PHE
TYR ILE GLU LEU ASP GLN GLN LEU ASN ASP LEU GLU ALA CYS VAL MET GLN
GLU GLU ARG VAL GLY GLU THR PRO LEU MET ASN ALA ASP SER ILE LEU ALA
VAL LYS LYS TYR PHE ARG ARG ILE THR LEU TYR LEU THR GLU LYS LYS TYR
SER PRO CYS ALA TRP GLU VAL VAL ARG ALA GLU ILE MET ARG SER PHE SER
LEU SER ILE ASN LEU GLN LYS ARG LEU LYS SER LYS GLU.

4. A hybrid vector according to claim 1, wherein the DNA sequence codes for the hybrid interferon polypeptide "B₁D₂B₃D₄" having the formula CYS ASP LEU PRO GLN THR HIS SER LEU GLY ASN ARG ARG ALA LEU ILE LEU
LEU ALA GLN MET ARG ARG ILE SER PRO PHE SER CYS LEU LYS ASP ARG HIS
ASP PHE GLU PHE PRO GLN GLU GLU PHE ASP ASP LYS GLN PHE GLN LYS ALA
GLN ALA ILE SER VAL LEU HIS GLU MET ILE GLN GLN ILE PHE ASN LEU PHE
THR THR LYS ASP SER SER ALA ALA TRP ASP GLU ASP LEU LEU ASP LYS PHE
CYS THR GLU LEU TYR GLN GLN LEU ASN ASP LEU GLU SER CYS VAL MET GLN
GLU VAL GLY VAL ILE GLU SER PRO LEU MET TYR GLU ASP SER ILE LEU ALA
VAL ARG LYS TYR PHE GLN ARG ILE THR LEU TYR LEU THR GLU LYS LYS TYR
SER SER CYS ALA TRP GLU VAL VAL ARG ALA GLU ILE MET ARG SER LEU SER
LEU SER THR ASN LEU GLN GLU ARG LEU ARG ARG LYS GLU.

5. A hybrid vector according to claim 1, wherein the DNA sequence codes for the hybrid interferon polypeptide "B₁D₂D₃B₄" having the formula CYS ASP LEU PRO GLN THR HIS SER LEU GLY ASN ARG ARG ALA LEU ILE LEU
LEU ALA GLN MET ARG ARG ILE SER PRO PHE SER CYS LEU LYS ASP ARG HIS
ASP PHE GLU PHE PRO GLN GLU GLU PHE ASP ASP LYS GLN PHE GLN LYS ALA
GLN ALA ILE SER VAL LEU HIS GLU MET ILE GLN GLN ILE PHE ASN LEU PHE
THR THR LYS ASP SER SER ALA ALA TRP ASP GLU ASP LEU LEU ASP LYS PHE
CYS THR GLU LEU TYR GLN GLN LEU ASN ASP LEU GLU ALA CYS VAL MET GLN
GLU GLU ARG VAL GLY GLU THR PRO LEU MET ASN ALA ASP SER ILE LEU ALA
VAL LYS LYS TYR PHE ARG ARG ILE THR LEU TYR LEU THR GLU LYS LYS TYR
SER PRO CYS ALA TRP GLU VAL VAL ARG ALA GLU ILE MET ARG SER PHE SER
LEU SER ILE ASN LEU GLN LYS ARG LEU LYS SER LYS GLU.

6. A hybrid vector according to claim 1, wherein the DNA sequence codes for the hybrid interferon polypeptide "B₁D₂D₃D₄" having the formula CYS ASP LEU PRO GLN THR HIS SER LEU GLY ASN ARG ARG ALA LEU ILE LEU
LEU ALA GLN MET ARG ARG ILE SER PRO PHE SER CYS LEU LYS ASP ARG HIS
ASP PHE GLU PHE PRO GLN GLU GLU PHE ASP ASP LYS GLN PHE GLN LYS ALA
GLN ALA ILE SER VAL LEU HIS GLU MET ILE GLN GLN ILE PHE ASN LEU PHE
THR THR LYS ASP SER SER ALA ALA TRP ASP GLU ASP LEU LEU ASP LYS PHE
CYS THR GLU LEU TYR GLN GLN LEU ASN ASP LEU GLU ALA CYS VAL MET GLN
GLU GLU ARG VAL GLY GLU THR PRO LEU MET ASN ALA ASP SER ILE LEU ALA
VAL LYS LYS TYR PHE ARG ARG ILE THR LEU TYR LEU THR GLU LYS LYS TYR
SER PRO CYS ALA TRP GLU VAL VAL ARG ALA GLU ILE MET ARG SER LEU SER
LEU SER THR ASN LEU GLN GLU ARG LEU ARG ARG LYS GLU.

7. A hybrid vector according to claim 1, wherein the DNA sequence codes for the hybrid interferon polypeptide "B₁D₂B₃B₄" having the formula CYS ASP LEU PRO GLN THR HIS SER LEU GLY ASN ARG ARG ALA LEU ILE LEU
LEU ALA GLN MET ARG ARG ILE SER PRO PHE SER CYS LEU LYS ASP ARG HIS
ASP PHE GLU PHE PRO GLN GLU GLU PHE ASP ASP LYS GLN PHE GLN LYS ALA
GLN ALA ILE SER VAL LEU HIS GLU MET ILE GLN GLN ILE PHE ASN LEU PHE
THR THR LYS ASP SER SER ALA ALA TRP ASP GLU ASP LEU LEU ASP LYS PHE
CYS THR GLU LEU TYR GLN GLN LEU ASN ASP LEU GLU SER CYS VAL MET GLN
GLU VAL GLY VAL ILE GLU SER PRO LEU MET TYR GLU ASP SER ILE LEU ALA
VAL ARG LYS TYR PHE GLN ARG ILE THR LEU TYR LEU THR GLU LYS LYS TYR
SER SER CYS ALA TRP GLU VAL VAL ARG ALA GLU ILE MET ARG SER PHE SER -continued
LEU SER ILE ASN LEU GLN LYS ARG LEU LYS SER LYS GLU.

8. A microorganism cell transformed with a hybrid vector according to claim 1.

9. A transformed microorganism cell according to claim 8 wherein the microorganism is yeast.

10. A transformed microorganism cell according to claim 8 wherein the microorganism is a bacterium.

11. A transformed microorganism cell according to claim 8 wherein the microorganism is selected from the group consisting of *Escherichia coli* and *Saccharomyces cerevisiae*.

* * * * *

UNITED STATES PATENT AND TRADEMARK OFFICE
CERTIFICATE OF CORRECTION

PATENT NO. : 5,071,761

DATED : December 10, 1991

INVENTOR(S) : Francois Meyer, Albert Hinnen, Andreas Meister, Markus G. Grutter and Sefik Alkan It is certified that error appears in the above-identified patent and that said Letters Patent is hereby corrected as shown below:

On the cover page, item 73, Assignee:, should read -- CIBA-GEIGY Corporation, Ardsley, N.Y. --.

Signed and Sealed this

Thirtieth Day of March, 1993

*Attest:*

STEPHEN G. KUNIN

*Attesting Officer*     *Acting Commissioner of Patents and Trademarks*